US008029551B2

(12) United States Patent
Running et al.

(10) Patent No.: US 8,029,551 B2
(45) Date of Patent: Oct. 4, 2011

(54) FRACTURE FIXATION PLATE WITH COVER SHEATH

(76) Inventors: Donald E. Running, Warsaw, IN (US); Robert Courtney, Jr., Pierceton, IN (US); Jeffrey A. Farris, Berne, IN (US)

( * ) Notice: Subject to any disclaimer, the term of this patent is extended or adjusted under 35 U.S.C. 154(b) by 1375 days.

(21) Appl. No.: 11/328,619

(22) Filed: Jan. 10, 2006

(65) Prior Publication Data

US 2007/0173839 A1 Jul. 26, 2007

(51) Int. Cl.
*A61B 17/80* (2006.01)
(52) U.S. Cl. .......................................... 606/295; 606/71
(58) Field of Classification Search .................. 606/71, 606/280, 281, 70, 286, 287, 289, 295, 296
See application file for complete search history.

(56) References Cited

U.S. PATENT DOCUMENTS

| 3,741,205 | A | | 6/1973 | Markolf et al. |
| 3,842,825 | A | * | 10/1974 | Wagner ........................... 606/66 |
| 4,408,601 | A | | 10/1983 | Wenk |
| 4,488,543 | A | * | 12/1984 | Tornier ........................... 606/65 |
| 4,493,317 | A | | 1/1985 | Klaue |
| 4,506,662 | A | | 3/1985 | Anapliotis |
| 4,794,918 | A | | 1/1989 | Wolter ............................ 128/92 |
| 4,867,144 | A | | 9/1989 | Karas et al. |
| 5,006,120 | A | | 4/1991 | Carter |
| 5,041,113 | A | | 8/1991 | Biedermann et al. |
| 5,127,914 | A | * | 7/1992 | Calderale et al. ................ 606/65 |
| 5,304,180 | A | | 4/1994 | Slocum |
| 5,364,399 | A | | 11/1994 | Lowery et al. |
| 5,531,746 | A | | 7/1996 | Errico et al. |
| 5,607,426 | A | | 3/1997 | Ralph et al. |
| 5,709,686 | A | | 1/1998 | Talos et al. ..................... 606/69 |
| 5,807,396 | A | | 9/1998 | Raveh |

(Continued)

FOREIGN PATENT DOCUMENTS

CA 2174293 10/1997

(Continued)

OTHER PUBLICATIONS

European Patent Office, Notification of Transmittal of the International Search Report and the Written Opinion of the International Searching Authority, PCT/US2007/060144, dated Sep. 19, 2008.

*Primary Examiner* — Eduardo C Robert
*Assistant Examiner* — Ellen C Hammond
(74) *Attorney, Agent, or Firm* — Heslin Rothenberg Farley & Mesiti P.C.

(57) ABSTRACT

A fracture fixation plate with cover sheath having a head element that is rigidly connected to a plate element in an upwardly angled direction. The head element is anatomically shaped and includes medial and lateral sheath recesses wherein non-threaded bone screw holes and a threaded sheath screw hole are located. Cylindrical head bone screws are inserted through the sheath recess and oriented at set angles allowing for bone fragment fixation and fracture reduction. Medial and lateral sheath elements are placed within the boundaries of their respective sheath recesses and are secured with a sheath screw. The sheath elements contact the heads of the inserted bone screws restricting and maintaining their implanted positions. Alternative sheath elements with outreaching medial, lateral and distal fragment capture flanges may also be utilized. The plate element includes at least one longitudinal slot with several bone screw holes for use with pivotable spherical headed bone screws.

41 Claims, 21 Drawing Sheets

U.S. PATENT DOCUMENTS

| | | |
|---|---|---|
| 5,951,558 A | 9/1999 | Fiz ................................. 606/70 |
| 6,022,350 A | 2/2000 | Ganem |
| 6,096,040 A * | 8/2000 | Esser .............................. 606/280 |
| 6,152,927 A | 11/2000 | Farris et al. |
| 6,235,034 B1 * | 5/2001 | Bray ............................... 606/71 |
| 6,283,969 B1 | 9/2001 | Grusin et al. |
| 6,290,703 B1 | 9/2001 | Ganem |
| 6,358,250 B1 | 3/2002 | Orbay ............................. 606/69 |
| 6,364,882 B1 | 4/2002 | Orbay ............................. 606/69 |
| 6,440,135 B2 | 8/2002 | Orbay et al. ................... 606/69 |
| 6,508,819 B1 | 1/2003 | Orbay ............................. 606/69 |
| 6,595,993 B2 | 7/2003 | Donno et al. |
| 6,599,290 B2 | 7/2003 | Bailey et al. |
| 6,623,486 B1 | 9/2003 | Weaver et al. ................. 606/69 |
| 6,669,700 B1 | 12/2003 | Farris et al. |
| 6,712,820 B2 * | 3/2004 | Orbay ............................ 606/286 |
| 6,767,351 B2 | 7/2004 | Orbay et al. ................... 606/69 |
| 6,866,665 B2 | 3/2005 | Orbay ............................. 606/69 |
| 6,893,444 B2 | 5/2005 | Orbay ............................. 606/69 |
| 7,001,387 B2 | 2/2006 | Farris et al. |
| 7,090,676 B2 | 8/2006 | Huebner et al. |
| 7,128,744 B2 | 10/2006 | Weaver et al. |
| 7,153,309 B2 | 12/2006 | Huebner et al. |
| 7,250,053 B2 | 7/2007 | Orbay |
| 7,276,070 B2 | 10/2007 | Muckter |
| 7,294,130 B2 | 11/2007 | Orbay |
| 7,341,589 B2 | 3/2008 | Weaver et al. |
| 2003/0078583 A1 | 4/2003 | Biedermann et al. |
| 2003/0105461 A1 | 6/2003 | Putnam ........................... 606/69 |
| 2003/0135213 A1 * | 7/2003 | LeHuec et al. .................. 606/69 |
| 2004/0102775 A1 | 5/2004 | Huebner ......................... 606/69 |
| 2004/0102778 A1 | 5/2004 | Huebner et al. ................ 606/71 |
| 2004/0153073 A1 | 8/2004 | Orbay |
| 2004/0193163 A1 | 9/2004 | Orbay |
| 2004/0210217 A1 * | 10/2004 | Baynham et al. ............... 606/61 |
| 2004/0220566 A1 | 11/2004 | Bray ............................... 606/61 |
| 2004/0225291 A1 * | 11/2004 | Schwammberger et al. ... 606/71 |
| 2004/0260292 A1 | 12/2004 | Orbay et al. |
| 2004/0260293 A1 | 12/2004 | Orbay et al. |
| 2004/0260294 A1 | 12/2004 | Orbay et al. |
| 2004/0260295 A1 | 12/2004 | Orbay et al. |
| 2005/0085818 A1 * | 4/2005 | Huebner ......................... 606/69 |
| 2005/0159747 A1 | 7/2005 | Orbay |
| 2005/0187551 A1 | 8/2005 | Orbay et al. |
| 2005/0234458 A1 * | 10/2005 | Huebner ......................... 606/69 |
| 2006/0009771 A1 | 1/2006 | Orbay et al. |
| 2006/0041260 A1 | 2/2006 | Orbay |
| 2006/0235402 A1 * | 10/2006 | Celli et al. ...................... 606/69 |
| 2007/0088360 A1 | 4/2007 | Orbay et al. |

FOREIGN PATENT DOCUMENTS

| | | |
|---|---|---|
| CH | 675531 A5 | 10/1990 |
| DE | 3301298 A1 | 2/1984 |
| DE | 19542116 A1 | 5/1997 |
| DE | 9321544 U1 | 9/1999 |

* cited by examiner

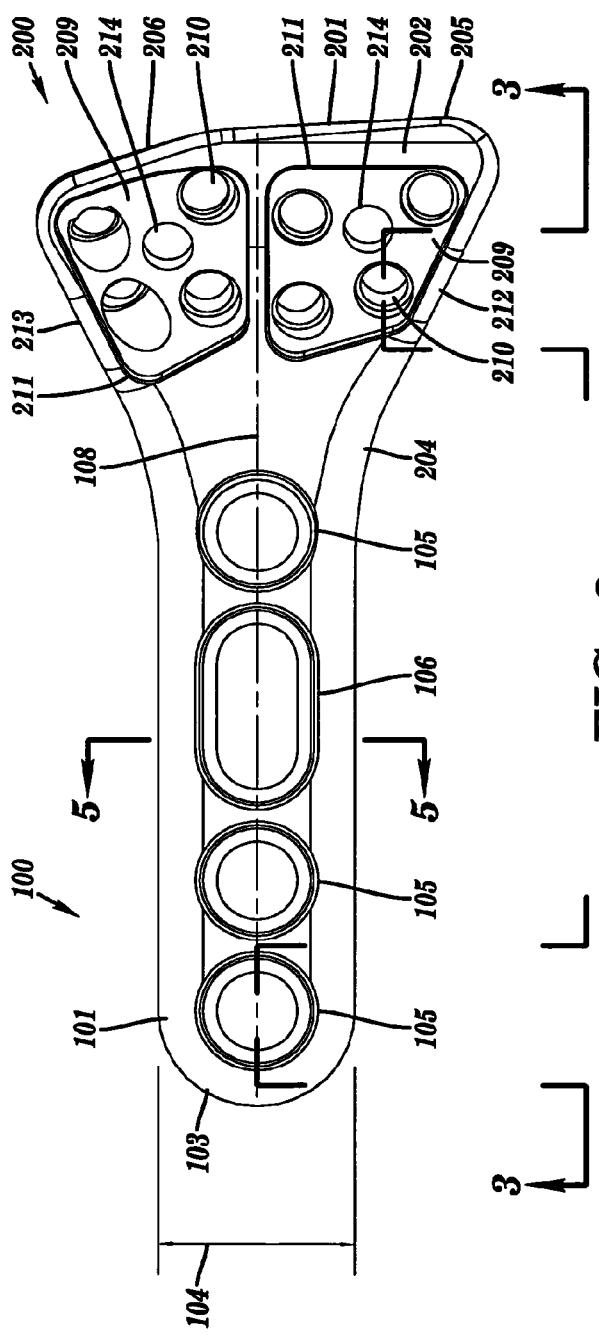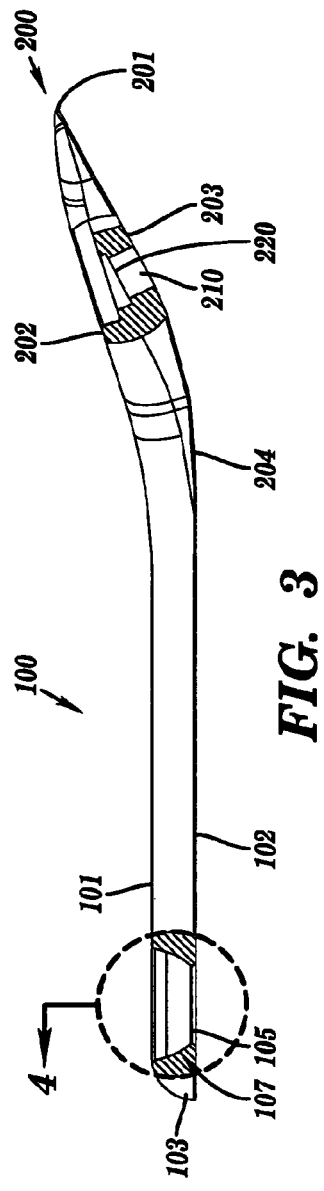
FIG. 2
FIG. 3

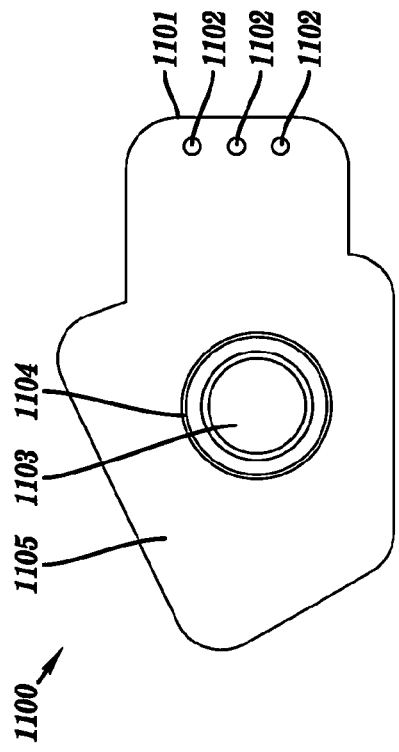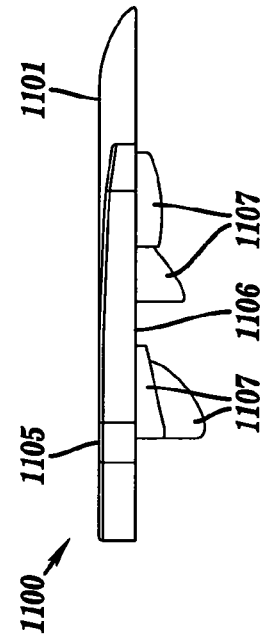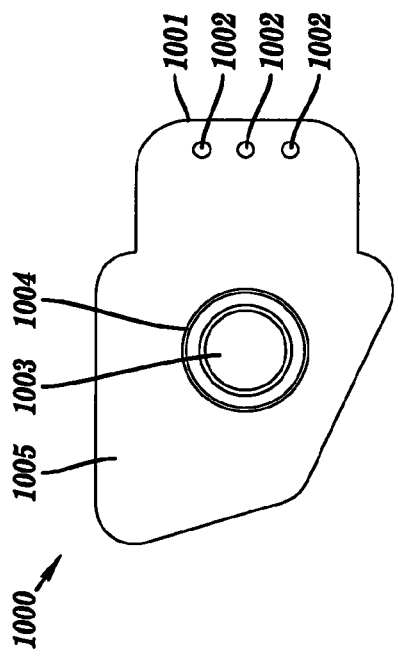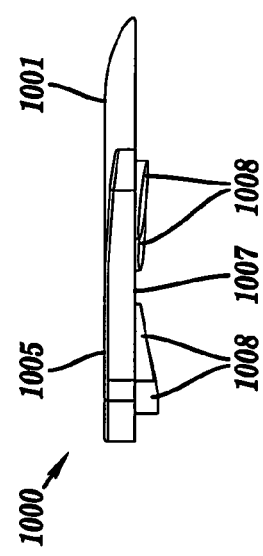

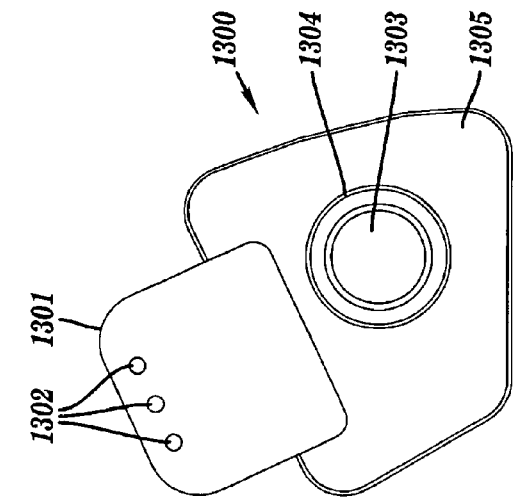
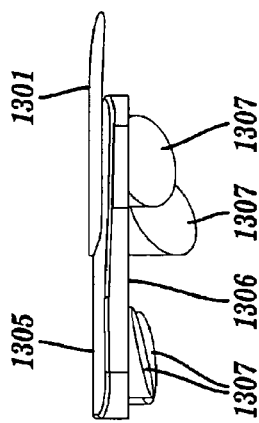
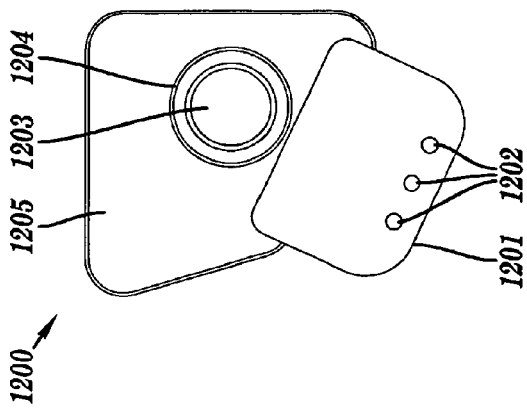
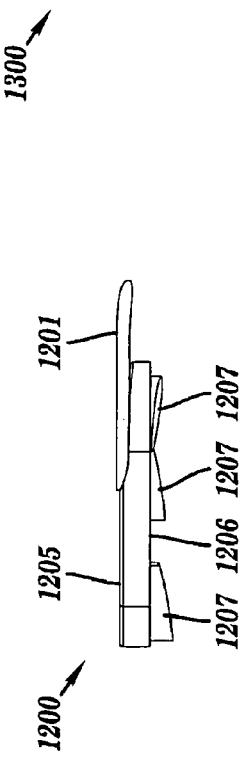
FIG. 26
FIG. 24
FIG. 25
FIG. 23

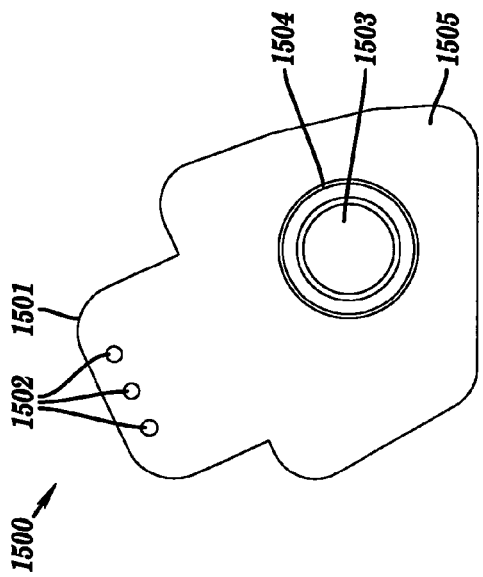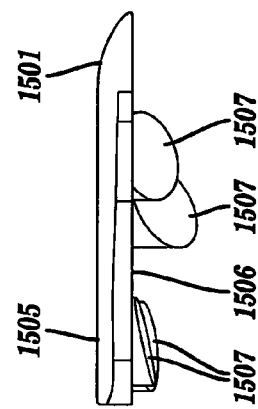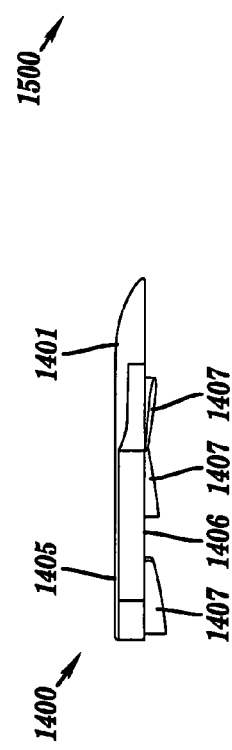
FIG. 30
FIG. 28
FIG. 29
FIG. 27

FRACTURE FIXATION PLATE WITH COVER SHEATH

FIELD OF THE INVENTION

This invention relates generally to implantable, surgical devices and the method for implantation and, in particular, to an improved surgical device to be used in the internal fixation of metaphyseal bone fractures.

BACKGROUND OF INVENTION

Proper securement of metaphyseal fractures in long bones is critical to ensuring restoration of pain free range of motion and full anatomic function. External fixation, casting and a variety of intra-operative techniques using various surgical implants have been used successfully to treat displaced metaphyseal fractures in long bones. Historically, open reduction and internal fixation, though highly invasive, has been the most successful treatment modality with these types of fractures. Various designs and shapes of metallic plates, pegs, wires and screws have been surgically implanted to stabilize and fix metaphyseal fractures. Examples of these surgical implants include U.S. Pat. Nos. 6,623,486, 6,866,665, 6,440,135, 6,364,882, 6,508,819, 6,358,250, 6,893,444, 6,767,351 and 6,712,820.

For a surgeon to be success in performing an open reduction and internal fixation of a metaphyseal fracture, the surgical implant must be designed to: allow for proper anatomical alignment restoration of the long bone, minimize soft-tissue disruption and allow for variable sturdy support of all displaced bone fragments. The prior art inventions do not include all of the necessary design attributes to allow the surgeon to accomplish all of these surgical goals.

Most prior art surgical implants utilize threaded head screws and/or threaded head pegs to secure displaced bone fragments. Implants utilizing this design concept are restricted to pre-set angular orientations for inserted screws and pegs, thereby inhibiting the surgeon from adequately securing loose bone fragments and restoring anatomical alignment. Further, the prior art surgical implants utilizing a threaded head design for screws and pegs does not allow the surgeon to draw or lag the bone fragments close to the implant. Resultant gaps between bone fragments and the implant increase the likelihood of decreased fracture site stabilization and incomplete fracture reduction. Possible post-operative complications resulting from such events include non-unions, malignment and reduced range of motion of the healed appendage. Additionally, the design of many prior art surgical implants may lead to other postoperative complications. The potential for tendonitis, tendon rupture and other soft-tissue impingement complications is increased by incongruent surfaces of an implant including exposed heads of fixation pegs and screws that have been inserted. The invention described herein addresses these and other design shortcomings of the prior art implants and provides the surgeon with the design attributes to allow for successful treatment of metaphyseal fractures in long bones.

SUMMARY OF THE INVENTION

The present invention provides a fracture fixation plate with cover sheath for use in the treatment of metaphyseal fractures of long bones. The purpose of the invention is to provide to the operating physician, a fracture fixation plate that allows for intra-operative flexibility, is designed to minimize soft-tissue impingement and allows for rigid stabilization and alignment of the fracture site and displaced bone fragments in the metaphyseal region of long bones.

In meeting these clinical objectives, the fracture fixation plate with cover sheath is generally comprised of a head element that typically includes a neck portion that rigidly joins to a plate element. A plurality of through holes are generally provided in the head element and the plate element. At least one slot is typically oriented along the longitudinal midline of the plate element. Bone screws are typically utilized in the plate element to secure the invention along the shaft of the fractured long bone, wherein bone screws or other types of bone fasteners may be inserted through the holes in the head element for the securement and alignment of any displaced bone fragments and achieve preferably adequate fracture reduction.

In another aspect, the present invention may also include an anatomically shaped head element with the most distal edge being wider in medial-lateral width in comparison to the more proximally located neck portion. At least one sheath recess is typically located within the top surface of the head element. Numerous angled, non-threaded and through bone fastener holes may be located within the boundaries of the sheath recess allowing for fixation of bone fragments and anatomic reconstruction of the fractured metaphysis. At least one threaded screw hole with a centerline perpendicular to the top surface of the head element may be located within the sheath recess.

In another aspect of the present invention, a plate element typically rigidly attaches to the proximal neck portion of the head element. The head angles in an upward direction relative to the plate with several through holes being generally located along the longitudinal midline of the plate. At least one longitudinal slot is positioned along the longitudinal midline of the plate element. The through holes of the plate element preferably allow for bone screws to be angled in multiple directions to maximize cortical bone purchase.

In yet another aspect of the present invention, at least one sheath element may be attached to the head element. The sheath fits within the sheath recess and may be secured by a threaded screw that engages both the sheath and head element. When in the recess, the sheath covers all of the heads of the inserted bone fasteners. The sheath may also include knobs or recesses located on the bottom surface, wherein when inserted, the knobs would typically project onto the opposing bone fastener head. Alternatively, the recesses would receive a protruding bone fastener head. These knobs and recesses are intended to substantially inhibit any movement by the bone fastener from its implanted position. The sheath, when joined with the head element, is preferably of minimal overall thickness, thereby giving the invention a low and congruent profile and preferably minimizing post-operative soft tissue impingement complications. Alternatively, the sheath may not fit with the sheath recess and may be secured to the head element by means other than a threaded screw including, but not limited to, a snap-lock, a locking hinge, slide rails, a press-fit lock, a spring lock or a modified threaded screw engagement. Preferably, the present invention includes a lateral sheath element and a medial sheath element. The lateral sheath element may sit within the sheath recess typically located in the lateral aspect of the head element and the medial sheath element may sit within the sheath recess typically located in the medial aspect of the head element.

In a further embodiment of the medial and lateral sheath elements, the distal side of the respective sheath may not be captured by the corresponding sheath recess and thereby extends past the distal edge of the head element creating a distal fragment capture flange. The distal fragment capture flange may have at least one through hole which is utilized to secure and align bone fragments located distally and not in close proximity to the through holes located in the head element. In yet a further embodiment of the medial and lateral sheath elements, said elements may be configured to include either a medial fragment capture flange, for the medial sheath element or a lateral fragment capture flange, for the lateral sheath element. The fragment capture flanges typically are not contained within the boundaries of their respective sheath recesses and usually extend beyond the medial or lateral edges of the head element. An alternative design would be wherein the medial and lateral sheaths are fully contained with their respective sheath recesses and the lateral fragment capture flange of the lateral sheath element preferably overlays onto the sheath and extends past the lateral edge of the head element with the medial fragment capture flange of the medial sheath element preferably overlaying onto the sheath and extending past the medial edge of the head element. The fragment capture flanges for both the medial and lateral sheath elements preferably include at least one through hole, which is utilized to secure and align either medially or laterally displaced bone fragments.

The present invention is used for treating metaphyseal fractures in long bones. Typically the plate element is initially secured to the shaft of the bone, preferably by inserting a spherical head bone screw through the longitudinally oriented slot, thereby allowing the fracture fixation plate to translate either proximally or distally. The plate element is preferably fixed to the bone following the plate element being generally aligned relatively parallel to the long axis of the bone with the neck portion of the head element being positioned over the bone fracture site. The displaced fracture is typically reduced by inserting at least one cylindrical head bone screw through a hole located in the head element and drawing the bone fragment in close proximity to the undersurface of the head element. Upon completion of the previous fracture reduction steps and while maintaining the set position of the fracture, additional holes may be drilled through the head element and plate element into the peripheral bone fracture fragments and shaft of the long bone respectively. The angles of the drill holes and inserted bone fasteners are typically determined by the location of the bone fragments and bone shaft. Following the insertion of all cylindrical head bone screws through the head element, the sheath may be set into the sheath recess with the bottom surface knobs preferably making contact with at least one of the inserted cylindrical head bone screw heads or in the alternative, the spherical head bone screw heads preferably projecting into the recesses located on the undersurface of the sheath whereby all motion of the inserted bone screws is substantially inhibited.

BRIEF DESCRIPTION OF THE DRAWINGS

The subject matter which is regarded as the invention is particularly pointed out and distinctly claimed in the claims at the conclusion of the specification. The features and advantages of the invention will be apparent from the following detailed description taken in conjunction with the accompanying drawings, which drawings illustrate several embodiments of the invention.

FIG. 2 is a top view of the subject invention.

FIG. 3 is a longitudinal cross-section view of the subject invention along line 3-3.

FIG. 18 is a medial perspective view of the medial sheath element with distal recessed fragment capture flange.

FIG. 19 is a lateral perspective view of the lateral sheath element with distal recessed fragment capture flange.

FIG. 20 is a top perspective view of the medial sheath element with distal recessed fragment capture flange.

FIG. 21 is a top perspective view of the lateral sheath element with distal recessed fragment capture flange.

FIG. 23 is a proximal perspective view of the medial sheath element with medial overlay fragment capture flange.

FIG. 24 is a distal perspective view of the lateral sheath element with lateral overlay fragment capture flange.

FIG. 25 is a top perspective view of the medial sheath element with medial overlay fragment capture flange.

FIG. 26 is a top perspective view of the lateral sheath element with lateral overlay fragment capture flange.

FIG. 27 is a proximal perspective view of the medial sheath element with medial recessed fragment capture flange.

FIG. 28 is a distal perspective view of the lateral sheath element with lateral recessed fragment capture flange.

FIG. 29 is a top perspective view of the medial sheath element with medial recessed fragment capture flange.

FIG. 30 is a top perspective view of the lateral sheath element with lateral recessed fragment capture flange.

DETAILED DESCRIPTION OF THE INVENTION

Figure 1:
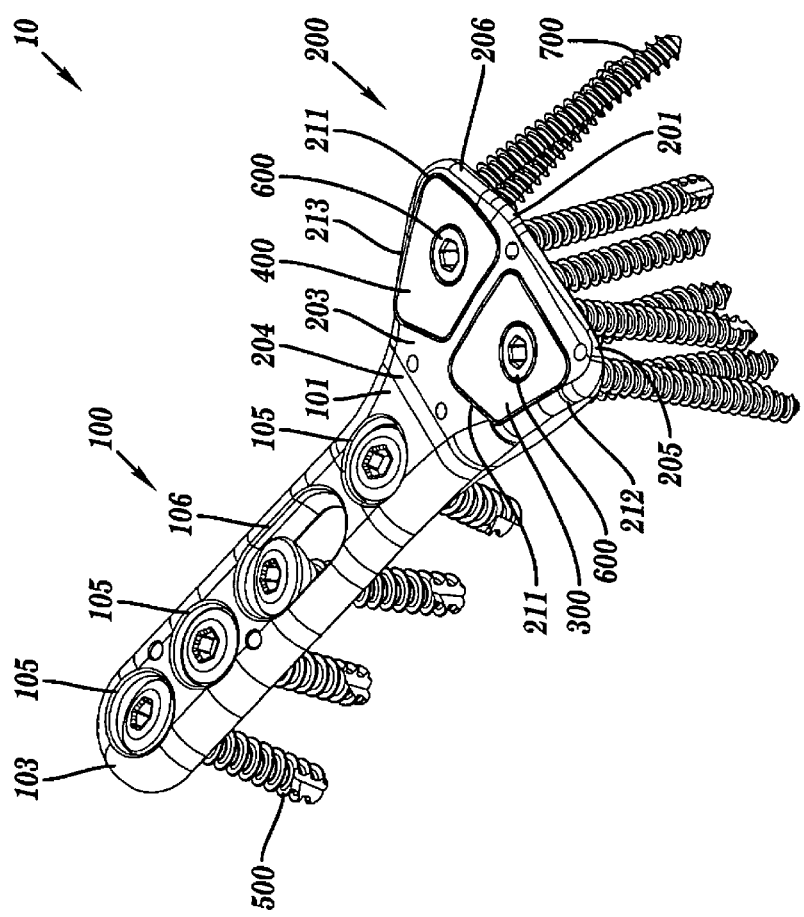
FIG. 1 is a distal end top perspective view of the subject invention.

FIG. 1 shows the general arrangement of a preferred embodiment of the fracture fixation plate with cover sheath 10. Generally, the fracture fixation plate with cover sheath 10 includes a plate element 100, a head element 200, a medial sheath 300, a lateral sheath 400, a bone fastener that may include a spherical head bone screw 500 and/or a cylindrical head bone screw 700 and a sheath screw 600. The various embodiments of the present invention, as described in greater detail below, result in the fracture fixation plate with cover sheath designed to allow for greater intraoperative flexibility and increased metaphyseal fracture stabilization.

With reference to FIGS. 2 and 3, the plate element 100 is comprised of a top surface 101 and an under surface 102 with a preferably mostly rounded proximal end 103. The medial-lateral width 104 of the plate element 100 is generally less than the medial-lateral width of the distal edge 201 of the head element 200. The plate element 100 preferably includes at least three therethrough fastener holes 105 with centerlines being about normal to the top surface 101 and along the longitudinal midline 108 of the plate element 100. At least one generally oval-shaped slot 106 is located along the longitudinal midline 108 with the slot 106 centerline being about normal to the top surface 101. Typically, the medial-lateral dimension of the slot 106 is approximately equal to the diameter of the fastener holes 105. The slot 106 allows for an inserted spherical head bone screw 500 to translate along the longitudinal midline 108 thereby providing for intra-operative flexibility in bone placement of the fracture fixation plate 10.

Figure 4:
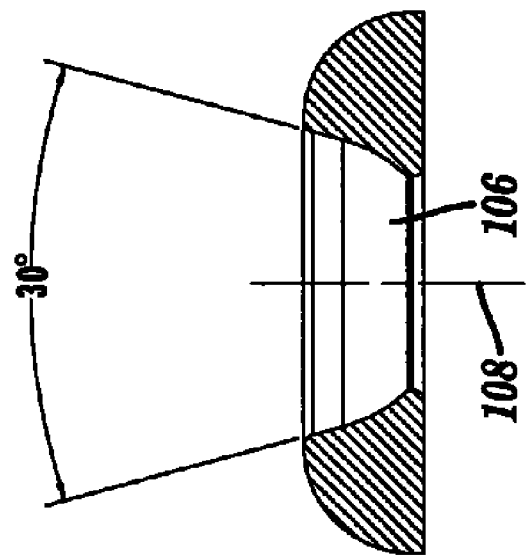
FIG. 4 is a partial longitudinal cross-section detailed view of the proximal fastener hole.
Figure 5:
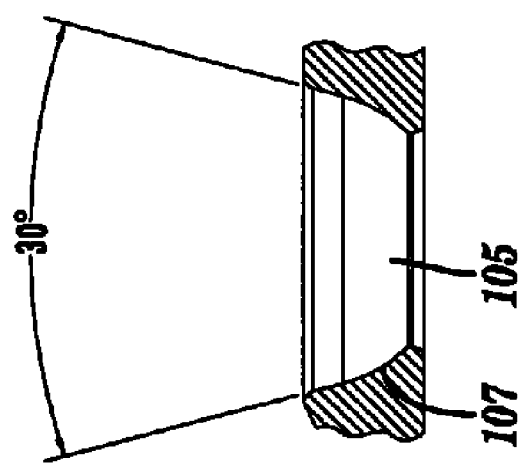
FIG. 5 is a partial medial-lateral cross-section detailed view of the slot along line 5-5.

As shown in FIG. 4, the fastener holes 105 may include a spherical seat area 107 allowing for the bone fastener, preferably the spherical head bone screw 500 to pivot in multiple directions with a preferable overall range of motion of thirty degrees relative to the longitudinal midline 108. FIG. 5 shows the spherical seat area of the slot 106 that may allow for the spherical head bone screw 500 to pivot predominantly in the medial-lateral direction with a preferable overall range of motion of thirty degrees relative to the longitudinal midline 108.

Referring again to FIGS. 2 and 3, the head element 200 includes a top surface 202, an under surface 203 and a neck portion 204. The head element 200 is angled typically at an acute angle relative to the plate element 100 with the distal edge 201 generally tapering in thickness distally to preferably minimize post-operative soft-tissue impingement complications. It is preferred for the medial-lateral width of the distal edge 201 to be equal or greater than the medial-lateral width of the neck portion 204. The distal edge 201 is preferably comprised of a medial portion 205 and a lateral portion 206. Preferably, the medial portion 205 and the lateral portion 206 of the distal edge 201 are oblique relative to the longitudinal midline 108. The general outer configuration of the head element 200 theoretically matches the anatomical shape of the bulbous end of a long bone. The head element 200 includes a set of non-threaded therethrough fastener holes 210. The fastener holes 210 are generally contained within the sheath recess 209 and arranged throughout the sheath recess 209 to preferably allow for the bone fasteners, typically a cylindrical head bone screw 700, to be inserted into the subchondral bone of the epiphysis and result in the desired bridging support for the head element 200. The fastener holes 210 may be counter-bored 220 creating a seat on which the inserted bone fastener, preferably the cylindrical head bone screw 700, may be positioned to substantially fix the insertion angle relative to the under surface 203. Preferably, the centerlines of the fastener holes 210 are oblique in two directions relative to each other. An alternative embodiment of the head element 200 may not include a sheath recess 209, whereby the heads of any inserted bone fastener would generally be covered by a one piece sheath cover (Not Shown) that matches the outer configuration of the head element 200. The one piece sheath cover may be secured to the head element 200 by the following means which include but are not limited to, the insertion of a single threadable screw that engages internal threads within the head element 200, multiple threadable screws that engage internal threads within the head element 200, a hinge member fixing the one piece cover sheath and the head element 200 on one side with a snap-like locking member or screw on the opposing side of the hinge member, or alternatively, a snap-like locking member on opposing sides of the one piece cover sheath that may lock within a corresponding opening located on the outside perimeter of the head element 200. Further alternative means for locking the one piece cover sheath to the head element 200 may include at least two parallel male or female rails located on the outer perimeter, either on the medial and lateral sides or the distal and proximal sides, of the head element 200 that preferably would match with the corresponding female or male rails located on the outer edges of the one piece cover sheath, or alternatively, the one piece cover sheath being generally configured with a key-like member allowing for proper alignment, and a coupling means with securement typically being achieved by press fit, spring lock or threaded screw engagement means.

As shown in FIGS. 1 and 2, a sheath recess 209 may be located on the medial aspect 212 and the lateral aspect 213 of the head element 200 allowing for the insertion of generally, the medial sheath 300 and lateral sheath 400. The sheath recesses 209 of the preferred embodiment are defined by a raised boundary 211. The raised boundary 211 for each sheath recess typically does not transect across the longitudinal midline 108 and is generally comprised of four sides. Wherein the distal boundaries extend in a generally medial-lateral direction in relatively close proximity to the distal edge 201. The midline boundary for the two sheath recesses each run preferably parallel to the longitudinal midline 108. The proximal boundaries for the two sheath recesses extend in a generally angular fashion outwardly towards the medial and lateral sides respectively of the head element 200. The outer raised boundary 211 for the two recesses preferably track in almost parallel fashion the outer edges of the medial aspect 212 and the lateral aspect 213 respectively of the head element 200. At least one threaded hole 214 for receipt of the sheath screw 600 is located within the sheath recess 209 with a centerline being oriented about normal to the floor of the sheath recess 209. The sheath screw 600 may be threaded into the threaded hole 214 as described below, following the placement of the medial sheath 300 and lateral sheath 400 into their respective sheath recesses 209.

Figure 8:
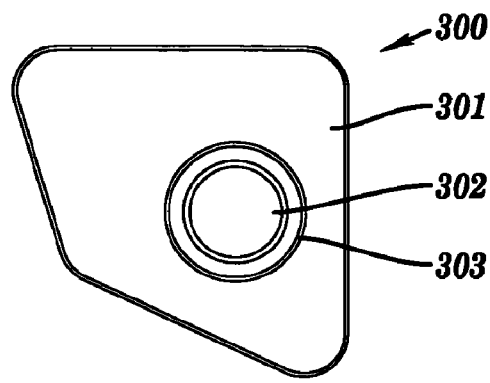
FIG. 8 is a top perspective view of the medial sheath element.
Figure 6:
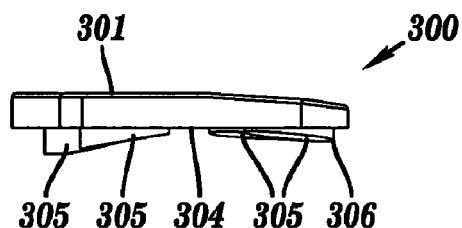
FIG. 6 is a distal end perspective view of the medial sheath element.
Figure 10:
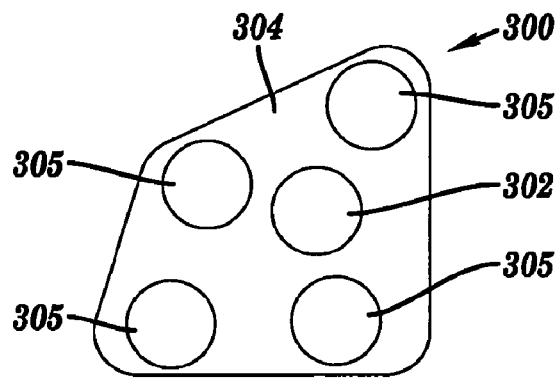
FIG. 10 is a bottom perspective view of the medial sheath element.
Figure 9:
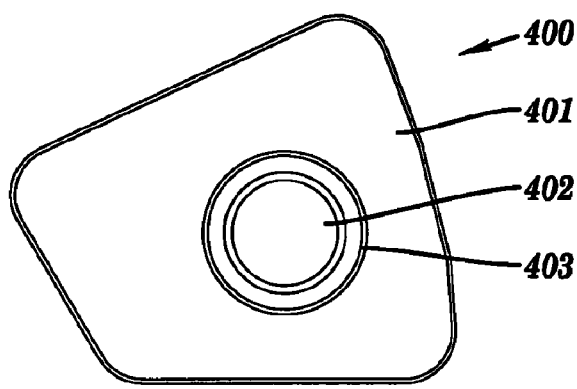
FIG. 9 is a top perspective view of the lateral sheath element.
Figure 7:
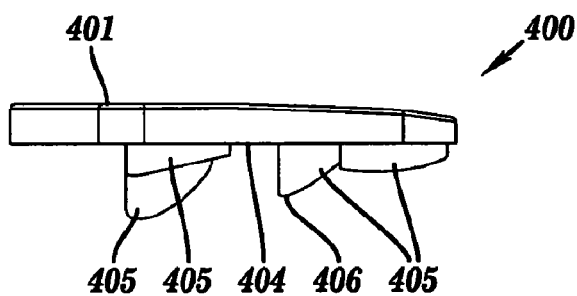
FIG. 7 is a distal end perspective view of the lateral sheath element.
Figure 11:
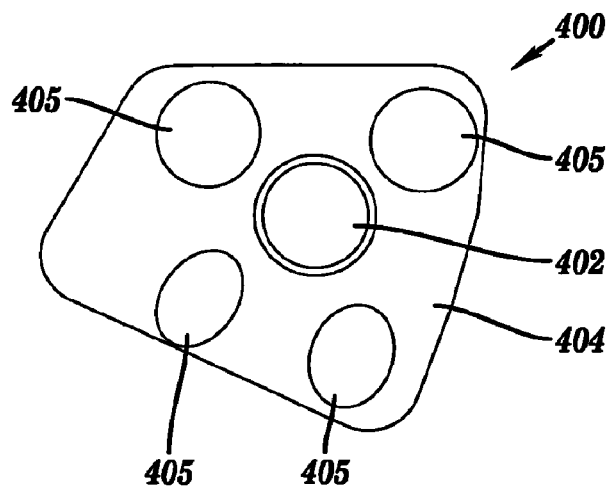
FIG. 11 is a bottom perspective view of the lateral sheath element.
Figure 14:
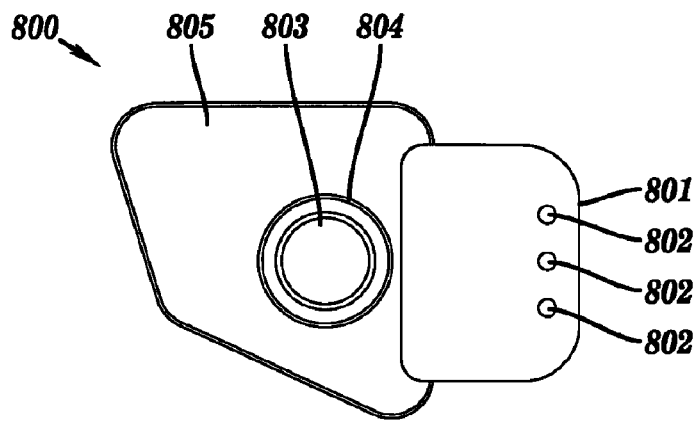
FIG. 14 is a top perspective view of the medial sheath element with distal overlay fragment capture flange.
Figure 12:
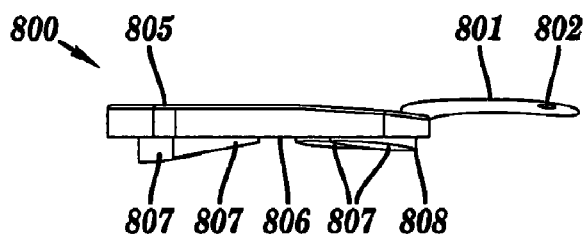
FIG. 12 is a medial perspective view of the medial sheath element with distal overlay fragment capture flange.
Figure 16:
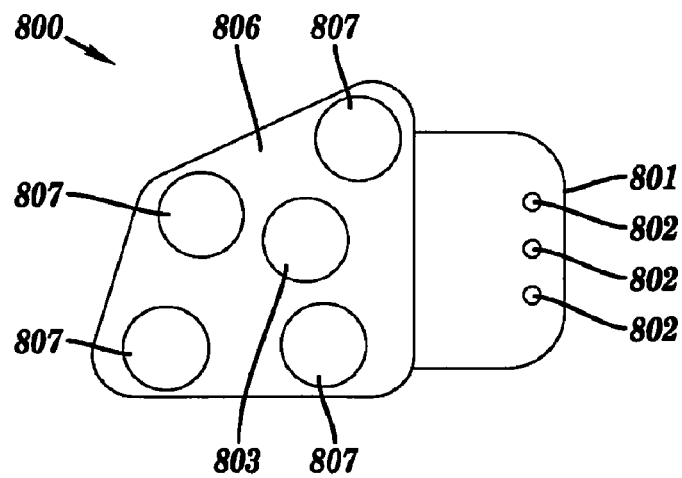
FIG. 16 is a bottom perspective view of the medial sheath element with distal overlay fragment capture flange.
Figure 15:
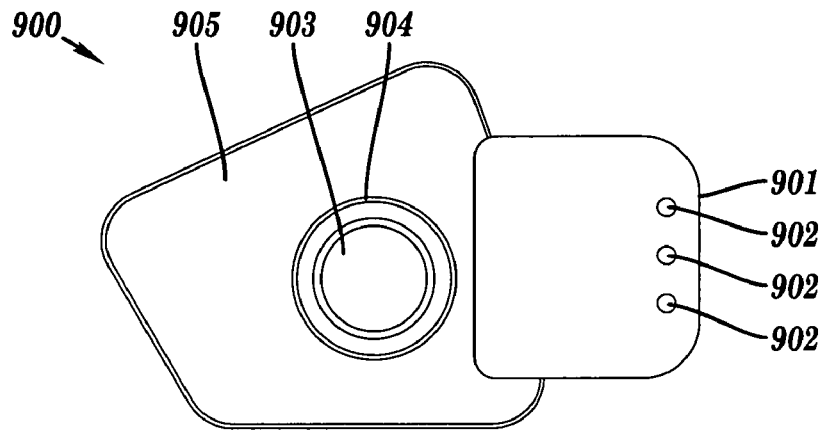
FIG. 15 is a top perspective view of the lateral sheath element with distal overlay fragment capture flange.
Figure 13:
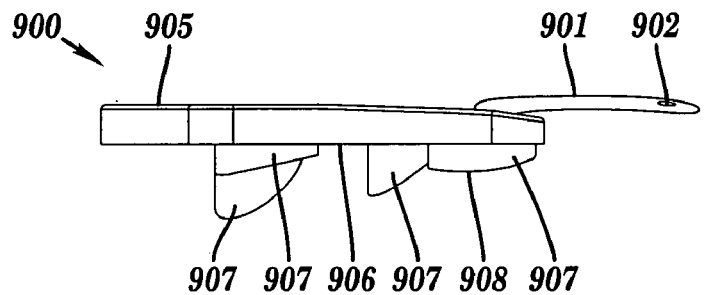
FIG. 13 is a lateral perspective view of the lateral sheath element with distal overlay fragment capture flange.
Figure 17:
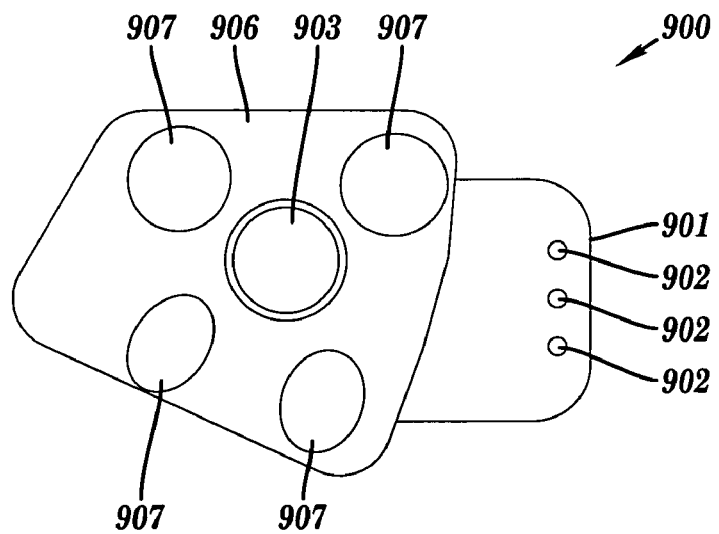
FIG. 17 is a bottom perspective view of the lateral sheath element with distal overlay fragment capture flange.

As provided above, the preferred embodiment of the fracture fixation plate with cover sheath 10 typically includes a medial sheath 300 and a lateral sheath 400 that are received into their respective sheath recesses 209. As seen in FIGS. 6 and 7, the medial and lateral sheaths 300, 400 are preferably comprised of a smooth and relatively flat top surface 301, 401 where when inserted into their respective sheath recesses 209 as shown in FIG. 1, a congruent surface, that will minimize disruption of any dissected soft-tissue, is formed. As shown in FIGS. 8 and 9, a threaded through hole 302, 402 is preferably located in the relative central aspect of the medial and lateral sheaths 300, 400. The threaded holes 302, 402 may have a counter-bore 303, 403 to allow for the inserted sheath screw head 601 to sit flush with the top surfaces 301, 401 when fully engaged. FIGS. 10 and 11 illustrate the bottom surfaces 304, 404 of the medial and lateral sheaths 300, 400 with at least one knob 305, 405 being present. Referring again to FIGS. 6 and 7, the knobs 305, 405 typically are cylinder-like members preferably projecting almost in a normal direction from the bottom surface 304, 404. When the medial and lateral sheaths 300, 400 are received into their respective sheath recesses 209, the irregular ends 306, 406 of the knobs 305, 405 may project onto the bone fastener head, preferably the cylindrical head bone screw head 701, to substantially inhibit any movement of the cylindrical head bone screw 700. An alternative embodiment of the medial and lateral sheaths 300, 400 may include a plurality of concave recesses (Not Shown) being preferably located on the bottom surface 304, 404. This embodiment, would enable the medial and lateral sheaths 300, 400 to generally receive the head of a bone fastener, preferably a spherical head bone screw 500, into the recess to substantially inhibit any movement of the spherical head bone screw 500 from its implanted position.

Referring now to FIGS. 12-17 there is shown further embodiments of the medial and lateral sheaths 300, 400. Specifically in FIGS. 12 and 13, the medial and lateral sheaths with a distal overlay fragment capture flange 800, 900 includes a distal fragment capture flange 801, 901 that may extend onto and beyond the distal edge 201. The medial and lateral sheaths with a distal overlay fragment capture flange 800, 900 may be configured and dimensioned to secure bone fragments that are located more distally than the distal edge 201. As shown in FIGS. 12-17, at least one (1) therethrough hole 802, 902 is provided in the distal overlay fragment capture flange 801, 901 to receive a bone fastener 500, 700 or k-wire (Not Shown) and a threaded through hole 803, 903 is preferably located in the relative central aspect of the medial and lateral sheaths with a distal overlay fragment capture flange 800, 900. The threaded holes 803, 903 may have a counter-bore 804, 904 to allow for the inserted sheath screw head 601 to sit flush with the top surface 805, 905 when fully engaged. The medial and lateral sheaths with a distal overlay fragment capture flange 800, 900 may be inserted into their respective sheath recesses 209 and are preferably contained within the raised boundary 211. The distal overlay fragment capture flange 801, 901 typically contacts the top surface 805, 905 and extends beyond the distal edge 201 to allow for the engagement of distally displaced bone fragments. The medial and lateral sheaths with a distal overlay fragment capture flange 800, 900 may on the bottom surface 806, 906 have at least one knob 807, 907. The knobs 807, 907 are typically cylinder-like members preferably projecting almost in a normal direction from the bottom surface 806, 906. When the medial and lateral sheaths with a distal overlay fragment capture flange 800, 900 are received into their respective sheath recesses 209, the irregular ends 808, 908 of the knobs 806, 906 may project onto the bone fastener head, preferably the cylindrical head bone screw head 701, to substantially inhibit any movement of the inserted cylindrical head bone screw 700. An alternative embodiment of the medial and lateral sheaths with a distal overlay fragment capture flange 800, 900 may include a plurality of concave recesses (Not Shown) being preferably located on the bottom surface 806, 906. This embodiment, would enable the medial and lateral sheaths with a distal overlay fragment capture flange 800, 900 to generally receive the head of a bone fastener, preferably a spherical head bone screw 500, into the recess to substantially inhibit any movement of the spherical head bone screw 500 from its implanted position.

Figure 22:
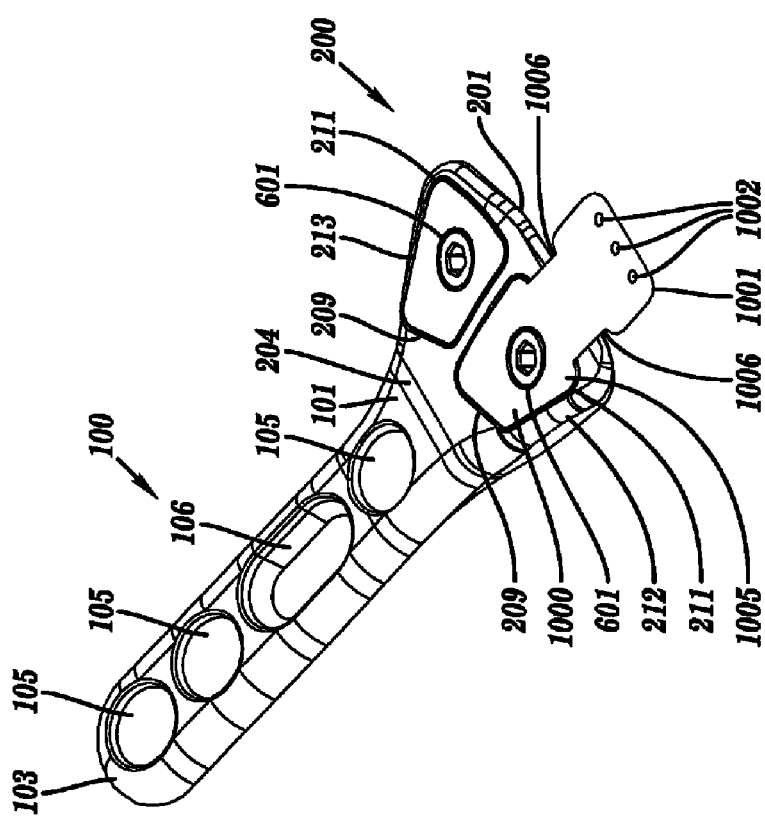
FIG. 22 is a distal end top perspective view of the subject invention with medial sheath element with distal recessed fragment capture flange.

Further embodiments of the medial sheath 300 and lateral sheath 400 are seen in FIGS. 18-22. Specifically in FIGS. 18 and 19, the medial and lateral sheaths with a distal recessed fragment capture flange 1000, 1100 includes a distal fragment capture flange 1001, 1101 that may extend beyond the distal edge 201. The medial and lateral sheaths with a distal recessed fragment capture flange 1000, 1100 may be configured and dimensioned to secure bone fragments that are located more distally than the distal edge 201. As shown in FIGS. 18-21, at least one (1) therethrough hole 1002, 1102 is provided in the distal recessed fragment capture flange 1000, 1100 to receive a bone fastener 500, 700 or k-wire (Not Shown) and a threaded through hole 1003, 1103 is preferably located in the relative central aspect of the medial and lateral sheaths with a distal recessed fragment capture flange 1000, 1100. The threaded hole 1003, 1103 may have a counter-bore 1004, 1104 to allow for the inserted sheath screw head 601 to sit flush with the top surface 1005, 1105 when fully engaged. The medial and lateral sheaths with a distal recessed fragment capture flange 1000, 1100 may be inserted into their respective sheath recesses 209. As seen in FIG. 22, the sheath recess 209 for the medial sheath with a distal recessed fragment capture flange 1000 may be modified by preferably removing the distal side of the raised boundary 211, whereby a passage 1006 is defined for the corresponding distal fragment capture flange 1001 to substantially sit. FIG. 22 further shows the distal fragment capture flange 1001 of the secured medial sheath with a distal recessed fragment capture flange 1000, being positioned to be generally congruent with the distal edge 201 and the top surface 1005 and extending in a distal direction to capture displaced bone fragments. The aforementioned design configuration may also be used in the lateral sheath with a distal recessed fragment capture flange 1100 and the corresponding lateral sheath recess 209 embodiments, such as shown in FIGS. 18-22. The bottom surfaces 1007, 1106 of the medial and lateral sheaths with a distal recessed fragment capture flange 1000, 1100 may also include the knob 1008, 1107 and the recess configuration (Not Shown) and their respective functionality as has been described above for the medial and lateral sheaths 300, 400 and shown in FIGS. 6, 7, 10 and 11.

Yet further embodiments of the medial and lateral sheaths 300, 400 are seen in FIGS. 23-26. Shown in these figures are the medial sheath with a medial overlay fragment capture flange 1200 and the lateral sheath with a lateral overlay fragment capture flange 1300. The medial sheath with a medial overlay fragment capture flange 1200 includes a medial fragment capture flange 1201 that may extend onto and beyond the edge of the medial aspect 212. The lateral sheath with a lateral overlay fragment capture flange 1300 also includes a lateral fragment capture flange 1301 that may extend onto and beyond the edge of the lateral aspect 213. The medial and lateral sheaths with their corresponding medial and lateral overlay fragment capture flanges 1200, 1300 may be configured and dimensioned to secure bone fragments that are located more medially and laterally respectively, relative to the head element 200. As shown in FIGS. 25 and 26, at least one (1) therethrough hole 1202, 1302 is provided in the medial and lateral overlay fragment capture flanges 1201, 1301 to receive a bone fastener 500, 700 or k-wire (Not Shown) and a threaded through hole 1203, 1303 is preferably located in the relative central aspect of the medial sheath with a medial overlay fragment capture flange 1200 and the lateral sheath with a lateral overlay fragment capture flange 1300. The threaded holes 1203, 1303 may have a counter-bore 1204, 1304 to allow for the inserted sheath screw head 601 to sit flush with the top surface 1205, 1305 when fully engaged. The medial sheath with a medial overlay fragment capture flange 1200 and the lateral sheath with a lateral overlay fragment capture flange 1300 may be inserted into their respective sheath recesses 209 and are preferably contained within the raised boundary 211. The medial and lateral overlay fragment capture flanges 1201, 1301 typically contact the top surfaces 1205, 1305 and extend beyond the corresponding outer edges of the medial aspect 212 and lateral aspect 213 respectively, to allow for the engagement of displaced bone fragments. The bottom surfaces 1206, 1306 of the medial sheath with a medial overlay fragment capture flange 1200 and the lateral sheath with a lateral overlay fragment capture flange 1300 may also include the knob 1207, 1307 and the recess configuration (Not Shown) and their respective functionality as has been described above for the medial and lateral sheaths 300, 400 and shown in FIGS. 6, 7, 10 and 11.

Figure 31:
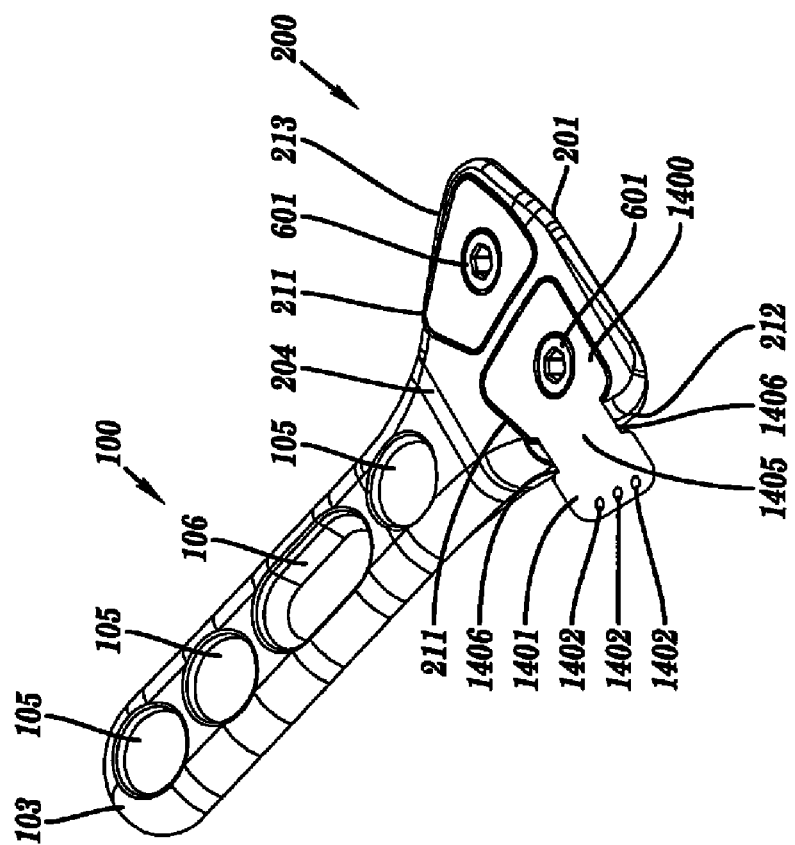
FIG. 31 is a distal end top perspective view of the subject invention with medial sheath element with medial recessed fragment capture flange.

Referring now to FIGS. 27-31, there is shown further embodiments of the medial and lateral sheaths 300, 400. These figures show the medial sheath with a medial recessed fragment capture flange 1400 and the lateral sheath with a lateral recessed fragment capture flange 1500. The medial sheath with a medial recessed fragment capture flange 1400 includes a medial fragment capture flange 1401 that may extend beyond the edge of the medial aspect 212. The lateral sheath with a lateral recessed fragment capture flange 1500 also includes a lateral fragment capture flange 1501 that may extend beyond the edge of the lateral aspect 213. The medial and lateral sheaths with their corresponding medial and lateral recessed fragment capture flanges 1400, 1500 may be configured and dimensioned to secure bone fragments that are located more medially and laterally respectively, relative to the head element 200. As shown in FIGS. 29 and 30, at least one (1) therethrough hole 1402, 1502 is provided in the medial and lateral recessed fragment capture flanges 1401, 1501 to receive a bone fastener 500, 700 or k-wire (Not Shown) and a threaded through hole 1403, 1503 is preferably located in the relative central aspect of the medial sheath with a medial recessed fragment capture flange 1400 and the lateral sheath with a lateral recessed fragment capture flange 1500. The threaded holes 1403, 1503 may have a counter-bore 1404, 1504 to allow for the inserted sheath screw head 601 to sit flush with the top surface 1405, 1505 when fully engaged. The medial sheath with a medial recessed fragment capture flange 1400 and the lateral sheath with a lateral recessed fragment capture flange 1500 may be inserted into their respective sheath recesses 209. As seen in FIG. 31, the sheath recess 209 for the medial sheath with a medial recessed fragment capture flange 1400 may be modified by preferably removing the medial side of the raised boundary 211, whereby a passage 1406 is defined for the corresponding medial fragment capture flange 1401 to substantially sit. FIG. 31 further shows the medial fragment capture flange 1401 of the secured medial sheath with a medial recessed fragment capture flange 1400, being positioned to be generally congruent with the outer edge of the medial aspect 212 and the top surface 1405 and extending medially to capture displaced bone fragments. The aforementioned design configuration may also be used in the lateral sheath with a lateral recessed fragment capture flange 1500 and the corresponding lateral sheath recess 209 embodiments, such as shown in FIG. 31. The bottom surfaces 1406, 1506 of the medial sheath with a medial recessed fragment capture flange 1400 and the lateral sheath with a lateral recessed fragment capture flange 1500 may also include the knob 1407, 1507 and the recess configuration (Not Shown) and their respective functionality as has been described above for the medial and lateral sheaths 300, 400 and shown in FIGS. 6, 7, 10 and 11.

Figure 32:
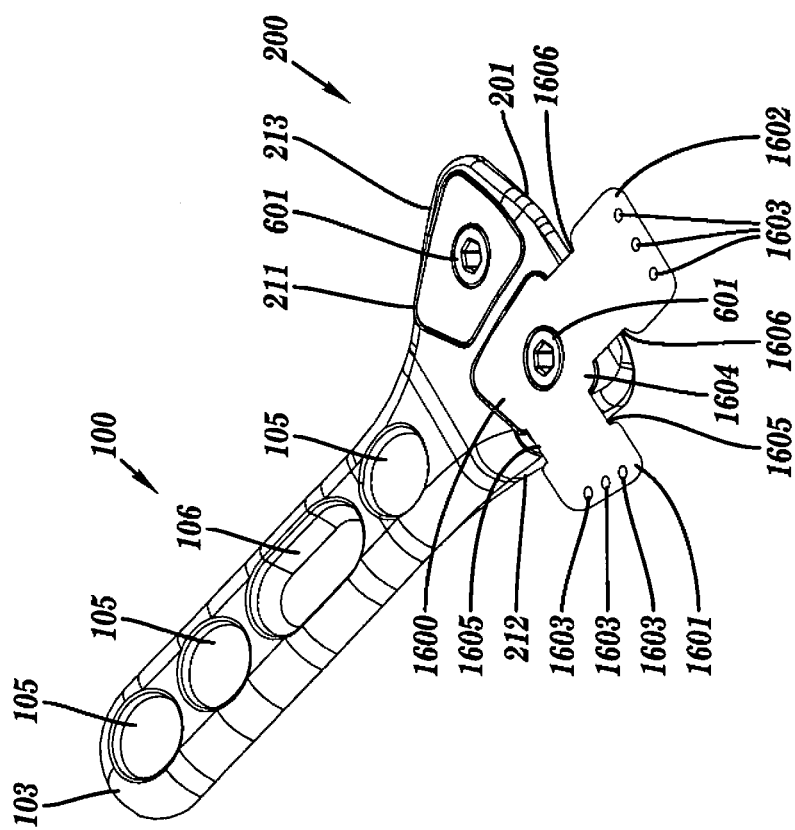
FIG. 32 is a distal end top perspective view of the subject invention with a medial sheath element with medial and distal recessed fragment capture flanges.

A further embodiment of the medial sheath 300 and lateral sheath 400 is seen in FIG. 32. This figure shows the medial sheath with medial and distal recessed fragment capture flanges 1600 that includes a medial fragment capture flange 1601 and a distal fragment capture flange 1602. The medial fragment capture flange 1601 may extend beyond the edge of the medial aspect 212 and the distal fragment capture flange 1602 may be configured and dimensioned to secure bone fragments that are located more distally than the distal edge 201. As shown in FIG. 32, at least one (1) therethrough hole 1603 is provided in the medial and distal recessed fragment capture flanges 1601, 1602 to receive a bone fastener 500, 700 or k-wire (Not Shown). The medial sheath with medial and distal recessed fragment capture flanges 1600 has preferably a threaded screw hole located in its central aspect 1610 to allow for the insertion of the sheath screw 600 wherein the sheath screw head 601 when fully engaged, may sit flush with the top surface 1604. The medial sheath with medial and distal recessed fragment capture flanges 1600 may be inserted into its sheath recesses 209. The sheath recess 209 for the medial sheath with medial and distal recessed fragment capture flanges 1600 may be modified by preferably removing the medial side and distal side of the raised boundary 211, whereby two passages 1605, 1606 are defined for the corresponding medial fragment capture flange 1601 and distal fragment capture flange 1602 to substantially sit. The medial fragment capture flange 1601 and distal fragment capture flange 1602 of the secured medial sheath with medial and distal recessed fragment capture flanges 1600 are typically positioned to be generally congruent with the outer edge of the medial aspect 212, the distal edge 201 and the top surface 1604. Though not shown herein, the aforementioned design configuration may also be used and configured as a lateral sheath with lateral and distal recessed fragment capture flanges with the corresponding lateral recess 209 being modified as stated herein to function in identical fashion as the medial sheath with medial and distal recessed fragment capture flanges 1600 as shown in FIG. 32. The bottom surface of the medial sheath with medial and distal recessed fragment capture flanges 1600 may also include the knob (Not Shown) and the recess configuration (Not Shown) and their respective functionality as has been described above for the medial and lateral sheaths 300, 400, as depicted in FIGS. 6, 7, 10 and 11.

Figure 33:
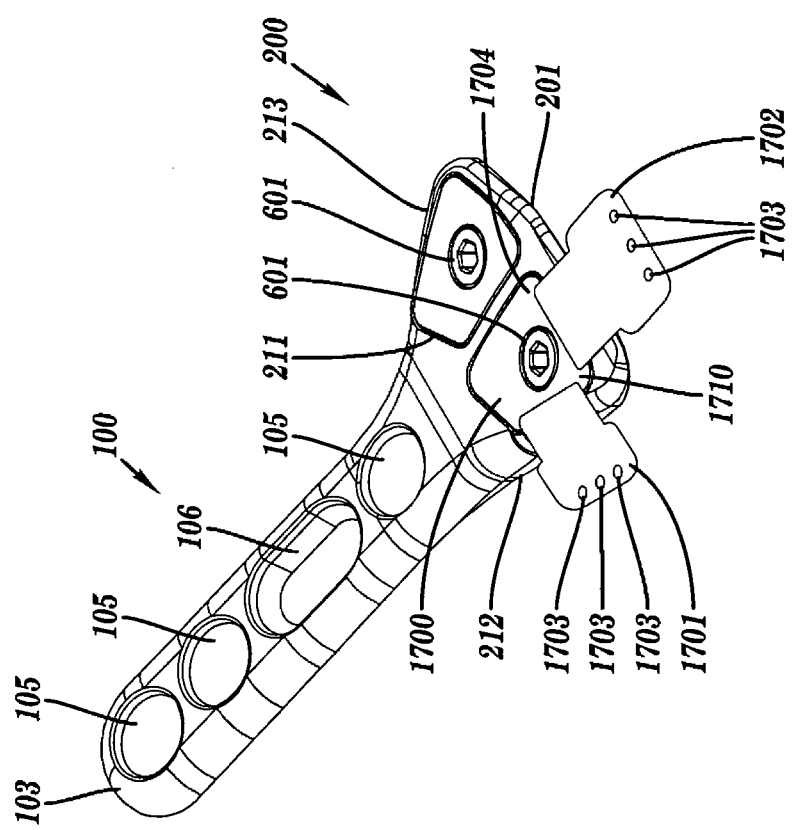
FIG. 33 is a distal end top perspective view of the subject invention with medial sheath element with medial and distal overlay fragment capture flanges.

Another embodiment of the medial sheath 300 and lateral sheath 400 is seen in FIG. 33, wherein this figure shows the medial sheath with medial and distal overlay fragment capture flanges 1700 that includes a medial fragment capture flange 1701 and a distal fragment capture flange 1702. The medial fragment capture flange 1701 may extend onto and beyond the edge of the medial aspect 212 and the distal fragment capture flange 1702 may extend onto and beyond the distal edge 201 to secure bone fragments that are located more distally than the distal edge 201. As shown in FIG. 33, at least one (1) therethrough hole 1703 is provided in the medial and distal overlay fragment capture flanges 1701, 1702 to receive a bone fastener 500, 700 or k-wire (Not Shown). The medial sheath with medial and distal overlay fragment capture flanges 1700 has preferably a threaded screw hole located in its central aspect 1710 to allow for the insertion of the sheath screw 600 wherein the sheath screw head 601 when fully engaged may sit flush with the top surface 1704. The medial sheath with medial and distal overlay fragment capture flanges 1700 may be inserted into its sheath recesses 209 and is preferably contained within the raised boundary 211. Though not shown herein, the aforementioned design configuration may also be used and configured as a lateral sheath with lateral and distal overlay fragment capture flanges with the corresponding lateral recess 209 being modified as stated herein to function in identical fashion as the medial sheath with medial additional overlay fragment capture flanges 1700 which is seen in FIG. 33. The bottom surface of the medial sheath with medial and distal overlay fragment capture flanges 1700 may also include the knob (Not Shown) and the recess configuration (Not Shown) and their respective functionality as has been described above for the medial and lateral sheaths 300, 400 and as shown in FIGS. 6, 7, 10 and 11.

As provided above, there have been described and illustrated several embodiments of the medial and lateral sheaths 300, 400 to be preferably inserted into the corresponding sheath recesses 209 of the head element 200. While numerous embodiments of the medial and lateral sheaths 300, 400 have been described, it is not intended that the invention and more specifically the medial and lateral sheaths 300, 400 be limited only to those expressly provided herein. Therefore, while the both the medial and lateral sheaths 300, 400 have been described herein as each being comprised of medial, lateral and distal overlay flanges and recessed flanges, it is intended and understood that the medial and lateral sheaths 300, 400 may be constructed of various combinations of the medial, lateral and distal overlay and recessed flanges. As an example, it is understood that a medial sheath 300 may be comprised of a recessed medial fragment capture flange in combination with an overlay distal fragment capture flange. As such, it is intended that the specification and the sheath elements 300, 400 described herein, be read to include every possible combination of sheath elements disclosed herein with the fracture fixation plates comprised of a plate element, and head element as disclosed herein.

Figure 34:
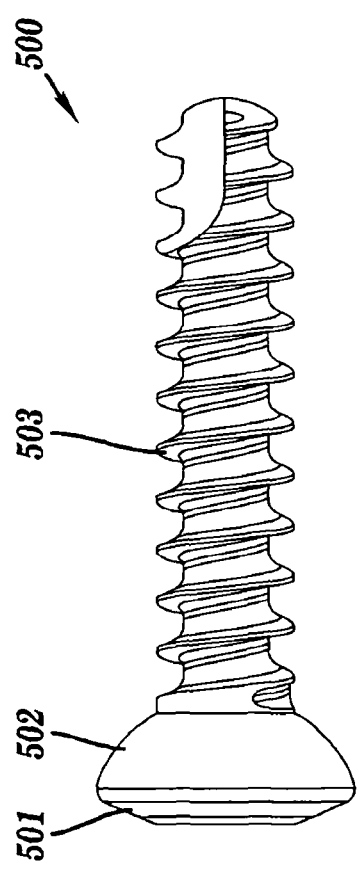
FIG. 34 is a side view of spherical head bone screw.

The spherical head bone screw 500 as seen in FIG. 34 is preferably used to fix the plate element 100 to the shaft of a long bone. Additionally, the spherical head bone screw 500 may be used in conjunction with the head element 200 and inserted through the fastener holes 210 to secure bone fragments and reduce the metaphyseal bone fracture. The bone screw 500 is typically available in various lengths. The length of spherical head bone screw 500 utilized is usually dependent upon the size and orientation of the shaft of the bone and in the displaced bone fragments. The screw head 501 typically has a generally hexagonal shaped indention on the top that matches the insertion tool head (Not Shown) and is relatively flat. The undersurface 502 of the screw head is generally spherical in shape to generally allow for multi-direction pivoting of the spherical head bone screw 500 following insertion into the fastener holes 105 in the plate element 100. The threads 503 are machined to allow the spherical head bone screw 500 to self-tap and preferably gain adequate boney purchase upon insertion.

Figure 35:
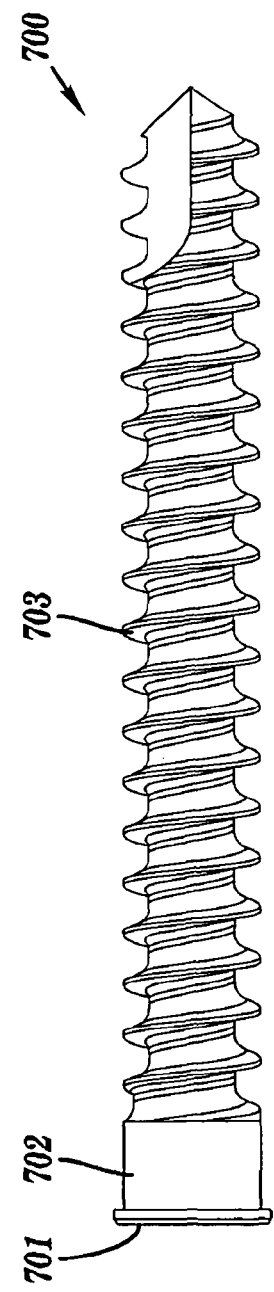
FIG. 35 is a side view of cylindrical head bone screw.

The cylindrical head bone screw 700 as seen in FIG. 35 is preferably used in conjunction with the head element 200 to secure bone fragments by insertion through the fastener holes 210. The cylindrical head bone screw 700 is typically available in various lengths. The length of cylindrical head bone screw 700 utilized is usually dependent upon the size and orientation of the displaced bone fragments. The cylindrical screw head 701 typically has a generally hexagonal shaped indention on the top that matches the insertion tool head (Not Shown) and is relatively flat. The sides and undersurface 702 of the screw head are relatively flat thereby allowing the cylindrical head bone screw 700 to comfortably sit within the counter bore 220 of the bone fastener holes 210 and at a relatively fixed angle. The threads 703 are machined to allow the cylindrical head bone screw 700 to self-tap and preferably gain adequate boney purchase in the displaced bone fragment.

Figure 36A:
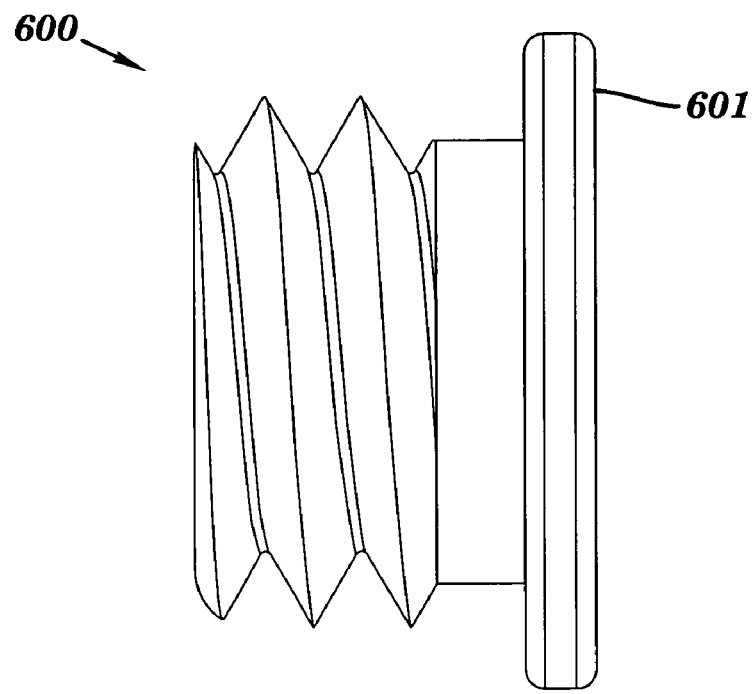
FIG. 36 is a side and top view of the sheath fixation screw.
Figure 36B:
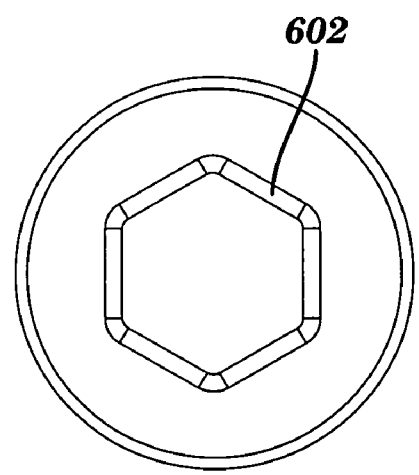

As shown in FIG. 36, the sheath screw 600 has a predominately flat head 601 and typically has the same generally hexagonal shaped indention 602 as the spherical head bone screw 500 and cylindrical head bone screw 700. The flat head 601 typically allows for the sheath screw 600, when fully inserted, to rest flush with the medial and lateral sheaths 300, 400 top surface 301, 401. The sheath screw 600 when threaded, engages both the medial and lateral sheaths 300, 400 and the head element 200 and conjoins the medial and lateral sheaths 300, 400 to the head element 200. Alternatively, the lateral and medial sheaths 300, 400 and the head element 200 may be secured to each other by means other than the sheath screw 600. These other means include, but are not limited to, multiple sheath screws, a hinge member fixing the medial and lateral sheaths 300, 400 and head element 200 on one side with a snap-like locking member or screw on the opposing side of the hinge member, or snap-like locking members on opposing sides of the medial sheath 300 and lateral sheath 400 that may lock within a corresponding opening located on the head element 200. Further alternative means for locking the medial or lateral sheaths 300, 400 to the head element 200 may include at least two parallel male or female rails located on the outer perimeter, either medial-lateral sides or distal-proximal sides, of the head element 200 that preferably would match with the corresponding female or male rails located on the medial and lateral sheaths 300, 400, or the medial and lateral sheaths 300, 400 being generally configured with a key-like member for alignment purposes that couples with a means of securement with the corresponding sheath recess 209 by a press fit, spring lock or threaded screw engagement means.

Figure 37:
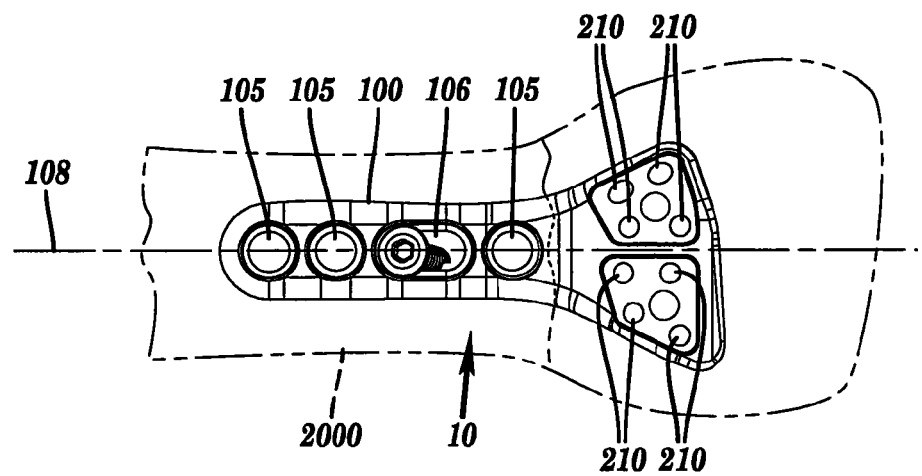
FIGS. 37-39 show the method used in treating a metaphyseal fracture of a long bone with the invention.
Figure 38:
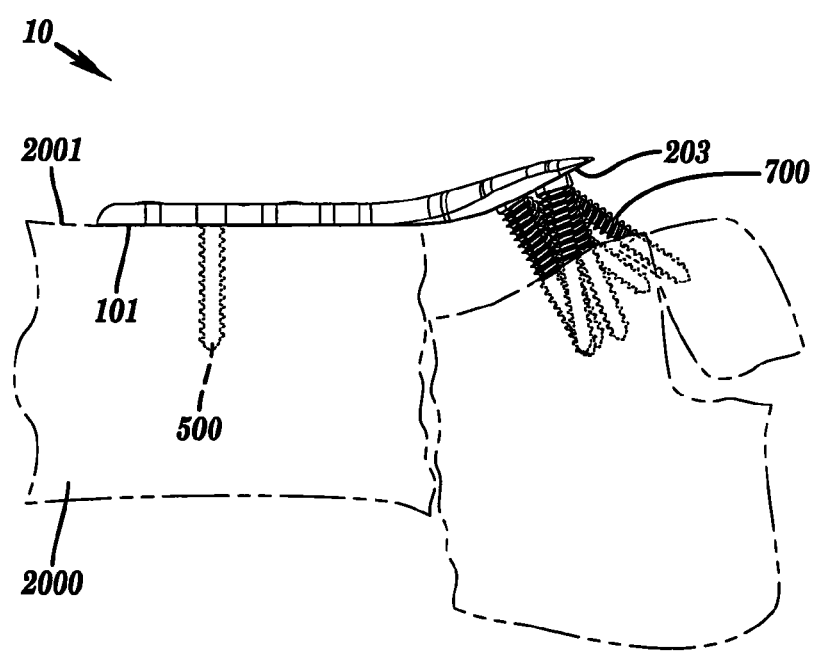
Figure 39:
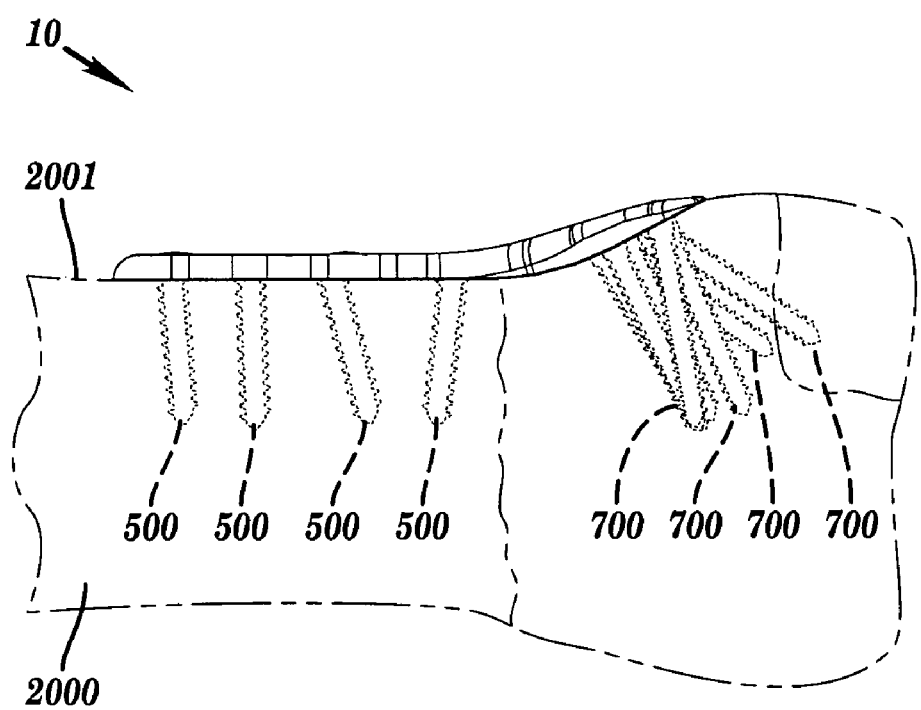

The preferred embodiment of the fracture fixation plate 10 may be used to treat metaphyseal and other similar types of fractures in long bones. Typically, the implantation method commences with a skin incision followed by careful dissection and distracted from the fracture site of surrounding soft tissue structures thereby exposing the bone fracture. As shown in FIGS. 37-39, the longitudinal midline 108 of the body element 100 is aligned along the diaphysis 2000 of the fractured bone. A spherical head bone screw 500 is inserted through the slot 106 threadingly engaging the cortex 2001 of the bone until the undersurface 101 contacts the cortex 2001. The fracture fixation plate 10 is translated either distally or proximally to optimize the alignment of the head element 200 with the fracture site. Following final alignment of the fracture fixation plate 10, several pilot holes may be drilled through the fastener holes 105 with spherical head bone screws 500 being inserted to threadingly engage the cortex 2001 thereby typically drawing the under surface 101 against the cortex 2001. Next, a drill guide (Not Shown) is placed within at least one of the fastener holes 205 situated within the sheath recess 209, with a pilot hole being drilled into at least one bone fragment. Following the drilling step, preferably at least one cylindrical head bone screw 700 is inserted through a fastener hole 205 at a fixed angle to threadingly engage the displaced bone fragments and draw the bone fragments towards the undersurface 203 thereby reducing the bone fracture. Following the securement of available bone fragments, the medial and lateral sheaths 300, 400 are positioned into their respective sheath recesses 209 and may be locked in place with the engagement of the sheath screw 600. For certain clinical cases wherein the bone fragments are more dispersed, the medial or lateral sheaths 300, 400 may be replaced by one of the numerous alternative sheath embodiments, which may include distal, medial and lateral fragment capture flanges, to secure outlying bone fragments.

Figure 40:
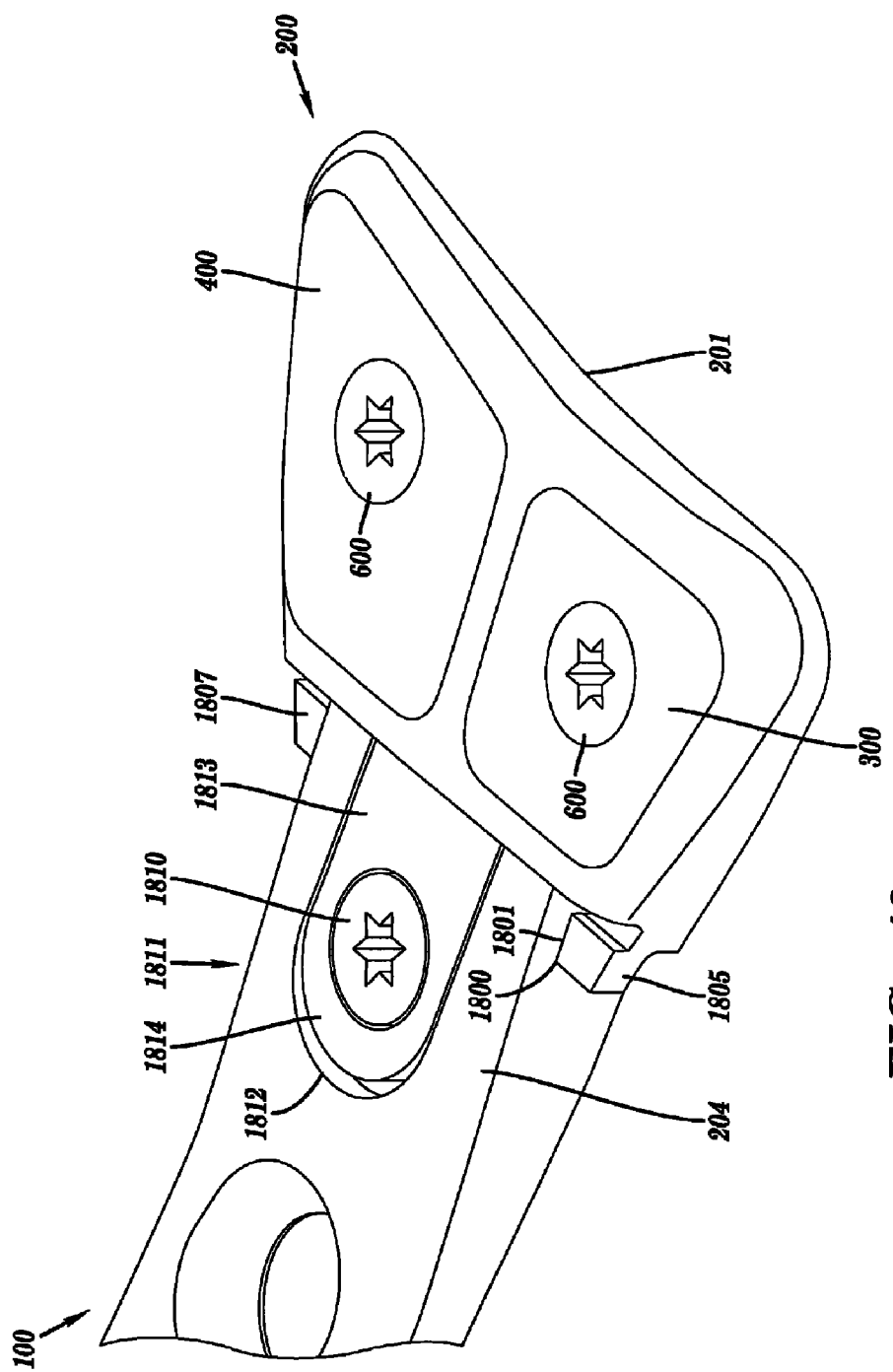
FIGS. 40-41 is an alternative embodiment of the invention with a medial-lateral translating head element.
Figure 41:
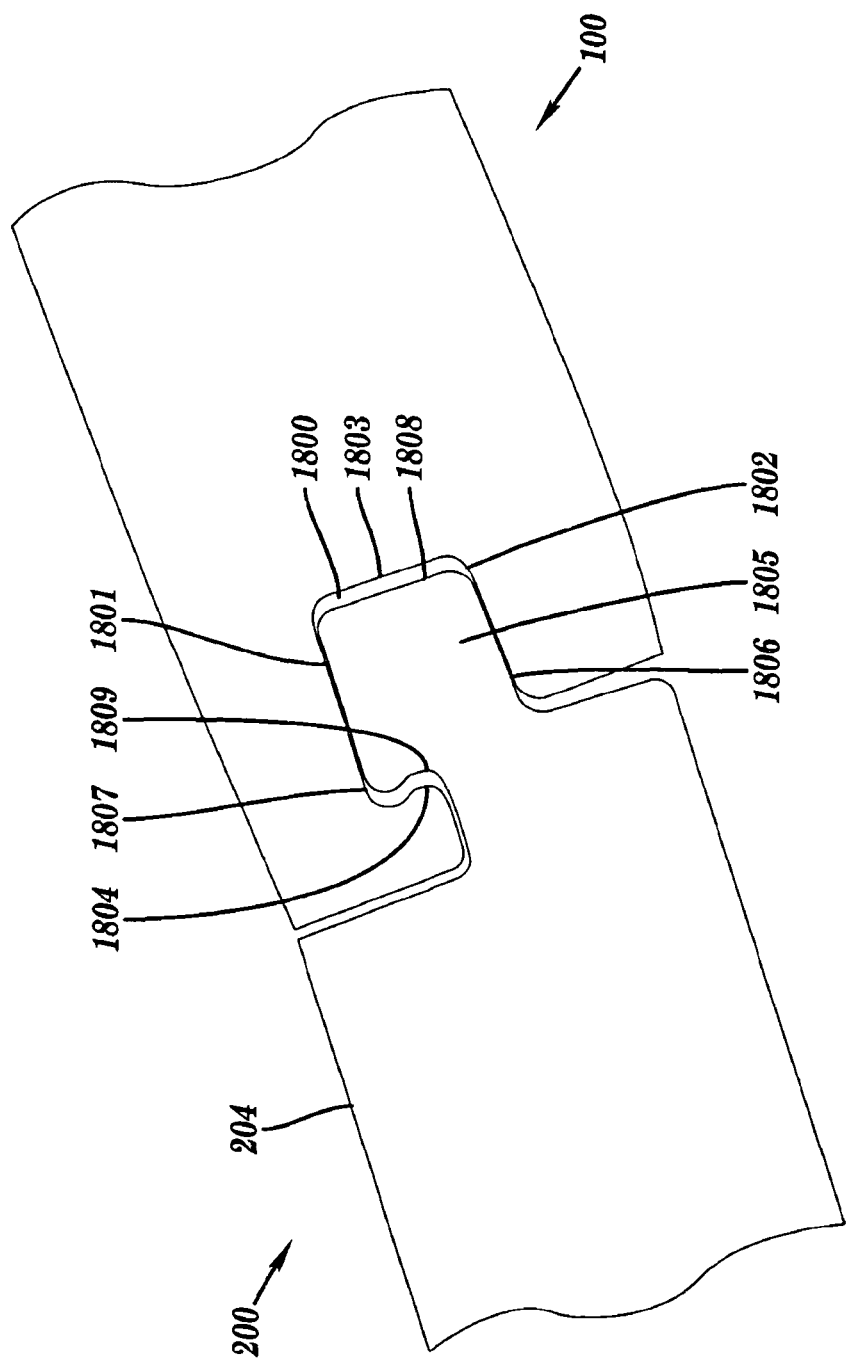

FIG. 40 illustrates another embodiment of the present invention, the fracture fixation plate with cover sheath 10, including a plate element 100 rigidly fixed to a head element 200 that includes a neck portion 204. As seen in FIGS. 40 and 41, the head element 200 of the alternative embodiment is modular and is transversely fixed to the neck portion 204 to allow for medial-lateral translation of the head element 200 relative to the plate element 100. The distal end of the neck portion 204 may be comprised of channel 1800 preferably running the entire medial-lateral width of the neck portion 204. The channel 1800 may typically be defined by an upper taper wall 1801, a lower taper wall 1802 and a connecting wall 1803, that may be defined by connecting the upper taper wall 1801 to the lower taper wall 1802 proximally. The upper taper wall 1801 may extend more distally than the lower taper wall 1802 and project in a downward direction to overhang the channel 1800 opening, thereby defining a distal capture hook 1804. The proximal edge of the head element 200 preferably includes a male member 1805 that generally runs the entire medial-lateral width of the head element 200. The male member 1805 may be defined by a tapered lower surface 1806, a tapered upper surface 1807 and a connecting surface 1808, that may be defined by connecting the upper taper surface 1807 to the lower taper surface 1806. Preferably at the distal end of the upper taper surface 1807, a medial-lateral running capture notch 1809 is located. To set the medial-lateral position of the head element 200, the male member 1805 may be slid into either the medial or lateral opening of the channel 1800 thereby also engaging the capture hook 1804 within the capture notch 1809 and then translating the head element 200 to the preferred medial-lateral location on the bone. Upon the application of a proximally directed load, the upper and lower tapered surfaces 1806, 1807 of the male member 1805 make contact with the upper and lower walls 1801, 1802 of the channel 1800 and the capture hook 1804 wedges into the capture notch 1809, locking the head element 200 in position. The directed load may be applied by several mechanisms, including, but not limited to, an offset locking screw 1810 that threadingly engages a locking plate 1811 that is comprised of a first end that is defined by a capture hook 1804, a plate member 1813 and a second end 1814 that sit within a corresponding mating slot 1812 located along the longitudinal midline 108 within the plate element 100, whereby as the locking screw 1810 is tightened, a proximally directed load is applied to the male member 1805 and capture notch 1809 securing the location of the head element 200. Benefits of having a modular head element 200 include intraoperative customization and inventory flexibility.

Figure 42:
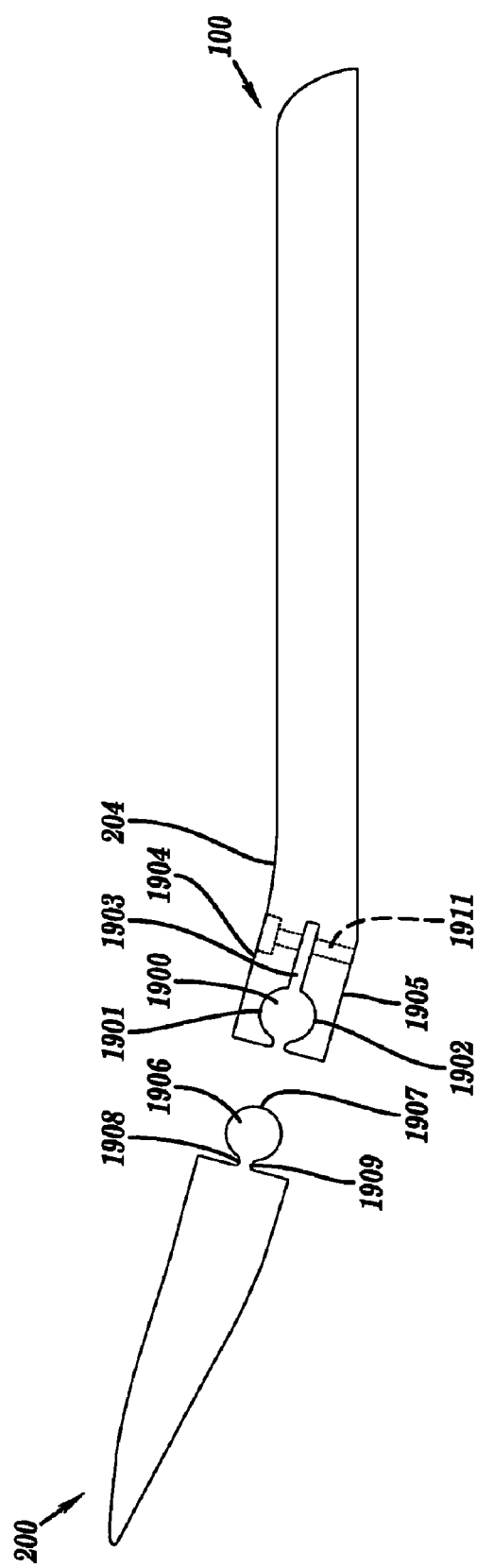
FIG. 42 is an alternative embodiment of the invention with a medial-lateral translating and anterior-posterior rotating head element.

FIG. 42 illustrates yet another embodiment of the present invention, the fracture fixation plate with cover sheath 10. The present invention 10 is comprised of a plate element 100 being rigidly fixed to a head element 200 that includes a neck portion 204. As shown in FIG. 42, the head element 200 of the alternative embodiment is modular and is fixed to the neck portion 204 to allow for medial-lateral translation of the head element 200 relative to the body element 100 and to allow for anterior-posterior rotation. The distal end of the neck portion 204 is comprised of concave semi-circular groove 1900 preferably running the entire medial-lateral width of the neck portion 204. The groove 1900 may be defined by an upper portion 1901 and a lower portion 1902 with the two portions being separated by a slot 1903 which bisects the neck portion 204 along a plane running parallel to the top surface 1904 and bottom surface 1905 of the neck portion 204. Preferably, a threaded therethrough hole 1911 may be located in the neck portion 204. The proximal edge of the head element 200 preferably includes a semi-circular mating member 1906 that generally runs the entire medial-lateral width of the head element 200. The mating member 1906 may be defined by a semi-circular rail 1907 with an upper channel 1908 and lower channel 1909 that run parallel to the rail 1907. To set the medial-lateral location and the anterior-posterior angle position of the modular head element 200, the mating member 1906 may be slid into either the medial or lateral opening of the groove 1900 with the ends of the upper portion 1901 and lower portion 1902 engaging the upper channel 1908 and the lower channel 1909 respectively, thereby allowing the head element 200 to translate to the preferred medial-lateral location on the bone and the head element 200 being rotated to the preferred anterior-posterior angle whereby the head element 200 is locked into place. The head element 200 may be locked by several mechanisms, including but not limited to, a loading screw 1910 that passes through the top surface 1904, the slot 1903 and the bottom surface 1905 and threadingly engages the top surface 1904 and bottom surface 1905 and places a resultant compressive load onto the rail 1907, the upper channel 1908 and the lower channel 1909 that substantially inhibits any further translational and anterior-posterior rotational movement of the head element 200.

Although the preferred embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A fracture fixation plate comprising:
    a head element having a top surface and under surface, said top surface having at least one sheath recess and a plurality of through holes in the at least one sheath recess adapted to receive bone fasteners;
    a plate element having a top surface and under surface, the plate element fixed to said head element and having a plurality of through holes adapted to receive bone fasteners; and
    at least one sheath member configured to mount into the at least one sheath recess in said head member, provide a congruent surface with the surface of the plate element that minimizes disruption of any dissected soft-tissue, and cover bone fasteners received in the plurality of through holes in the at least one sheath recess;
    wherein the at least one sheath member includes a bottom surface having a plurality of circular members each positioned to contact one of the bone fasteners received in the plurality of through holes in the at least one sheath recess, each of the plurality of circular members adapted to substantially inhibit any movement of one of the bone fasteners.

2. The fracture fixation plate of claim 1, wherein said head element is angled in an upward direction relative to the plate element.

3. The fracture fixation plate of claim 1, wherein said head element comprises a distal edge portion and a proximal neck portion.

4. The fracture fixation plate of claim 3, wherein said distal edge portion tapers in thickness.

5. The fracture fixation plate of claim 3,
    wherein said distal edge portion comprises a medial-lateral width; and wherein said proximal neck portion comprises a medial-lateral width; and wherein said medial-lateral width of said distal edge portion is greater than said medial-lateral width of said proximal neck portion.

6. The fracture fixation plate of claim 1, wherein at least one of said plurality of through holes in said plate element includes at least one longitudinal slot.

7. The fracture fixation plate of claim 1, wherein the at least one sheath recess in the top surface comprises at least two sheath recesses.

8. The fracture fixation plate of claim 1, wherein said plurality of through holes in the at least one sheath recess are longitudinally and laterally spaced within the at least one sheath recess.

9. The fracture fixation plate of claim 8, wherein at least one of said plurality of through holes in the at least one sheath recess has an oblique centerline relative to at least one of the other of the plurality of through holes in the at least one sheath recess.

10. The fracture fixation plate of claim 1, wherein said plurality of through holes in the at least one sheath recess includes at least one hole having a centerline about normal to a surface of said at least one sheath recess.

11. The fracture fixation plate of claim 1, wherein said plurality of through holes in the at least one sheath recess includes at least one hole having a centerline angled to a surface of said at least one sheath recess.

12. The fracture fixation plate of claim 1, wherein said plurality of circular members comprises a plurality of raised circular knobs; and wherein said at least one sheath member is configured to fixedly mount into the at least one sheath recess in said head element.

13. The fracture fixation plate of claim 12, wherein said sheath member comprises at least one through hole having a centerline about normal to a top surface of said sheath member.

14. The fracture fixation plate of claim 1, wherein the plurality of circular members each positioned to contact one of the bone fasteners comprises one of a plurality of projections each adapted to inhibit rotation of one of the bone fasteners and a plurality of recesses each adapted to inhibit rotation of one of the bone fasteners.

15. The fracture fixation plate of claim 1, wherein the plurality of circular members each positioned to contact one of the bone fasteners comprises a plurality of circular cylindrical knobs each of the knobs adapted to inhibit rotation of one of the bone fasteners.

16. The fracture fixation plate of claim 1, wherein the plurality of circular members each positioned to contact one of the bone fasteners comprises a plurality of circular concave recesses each recess adapted to inhibit rotation of one of the bone fasteners.

17. The fracture fixation plate of claim 1, wherein said plurality of circular members each adapted to substantially inhibit any movement of one of the bone fasteners comprises a plurality of circular members each adapted to prevent any movement of one of the bone fasteners.

18. The fracture fixation plate of claim 1, wherein said at least one sheath member comprises a fragment capture flange extending from said sheath member.

19. The fracture fixation plate of claim 18, wherein said fragment capture flange extends from an edge of said sheath member.

20. The fracture fixation plate of claim 1, wherein each the plurality of circular members comprises an end surface; and wherein the end surface of each of the plurality of circular members contacts a top surface of one of the bone fasteners to substantially inhibit any movement of the one of the bone fasteners.

21. The fracture fixation plate of claim 20, wherein the end surface of each of the plurality of circular members comprises an irregular end surface.

22. A fracture fixation plate system comprising:
a fixation plate comprising:
a head member having a top surface and an under surface, wherein said top surface includes at least one sheath recess, the at least one sheath recess having a plurality of through holes; and
a longitudinal body member fixed to said head element, the longitudinal body member having a top surface and under surface and a plurality of through holes;
a plurality of bone fasteners configured to secure the fixation plate to bone; and
at least one sheath member adapted to mount into the at least one sheath recess in said head member and provide a congruent surface with the top surface of the head member that minimizes disruption of any dissected soft-tissue, the at least one sheath member having a bottom surface having a plurality of circular members each positioned to contact one of the plurality of bone fasteners and substantially inhibit movement of one of the plurality of bone fasteners.

23. The fracture fixation plate system of claim 22, wherein the plurality of through holes in said longitudinal body member includes at least one slot oriented along a midline of said longitudinal body member.

24. The fracture fixation plate system of claim 22, wherein said head member is angled relative to said longitudinal body member.

25. The fracture fixation plate system of claim 22, wherein said head member comprises a distal edge, a lateral edge, a medial edge and a proximal neck, and wherein said proximal neck fixedly connects said head member to said longitudinal body member; and wherein said sheath member comprises a top surface, a bottom surface, and a bone fragment capture flange.

26. The fracture fixation plate system of claim 25, wherein said bone fragment capture flange includes at least one through hole.

27. The fracture fixation plate system of claim 25, wherein said distal edge comprises a first end and a second end, and wherein said lateral edge comprises a distal end and a proximal end, and wherein said medial edge comprises a distal end and a proximal end.

28. The fracture fixation plate system of claim 27, wherein said distal edge is longer than said proximal neck, and wherein said distal end of the medial edge is connected to the first end of said distal edge, and wherein said distal end of the lateral edge is connected to the second end of said distal edge, and wherein the medial edge and lateral edge are substantially equal in length, and wherein said medial edge and said lateral edge are angled relative to said distal edge, and wherein said medial edge and said lateral edge extend from said first end and said second end of said distal edge to connect to the proximal neck.

29. The fracture fixation plate system of claim 25, wherein said bone fragment capture flange extends from said sheath member.

30. The fracture fixation plate system of claim 25, wherein said bone fragment capture flange extends beyond said distal edge.

31. The fracture fixation plate system of claim 25, wherein said bone fragment capture flange extends beyond said medial edge.

32. The fracture fixation plate system of claim 25, wherein said bone fragment capture flange extends beyond said lateral edge.

33. The fracture fixation plate system of claim 25, wherein said bone fragment flange extends beyond at least one of the lateral edge and distal edge.

34. The fracture fixation plate system of claim 25, wherein said bone fragment flange extends beyond at least one of the medial edge and distal edge.

35. The fracture fixation plate system of claim 22, wherein said head member is substantially shaped to approximate a shape of a bulbous end of a long bone.

36. The fracture fixation plate system of claim 22, wherein said at least one sheath member is adapted to fixedly mount into the at least one sheath recess.

37. The fracture fixation plate system of claim 36, further comprising means for fixedly mounting said sheath member into said sheath recess.

38. The fracture fixation plate system of claim 22, wherein said sheath member covers said plurality of through holes in the at least one sheath recess.

39. The fracture fixation plate system of claim 22, wherein said plurality of circulars members comprises a plurality of raised circular knobs projecting from the bottom surface of the at least one sheath member.

40. The fracture fixation plate of claim 22, wherein each the plurality of circular members comprises an end surface; and wherein the end surface of each of the plurality of circular members contacts a top surface of one of the plurality of bone fasteners to substantially inhibit any movement of the one of the plurality of bone fasteners.

41. The fracture fixation plate of claim 40, wherein the end surface of each of the plurality of circular members comprises an irregular end surface.

* * * * *

UNITED STATES PATENT AND TRADEMARK OFFICE
CERTIFICATE OF CORRECTION

| | | |
|---|---|---|
| PATENT NO. | : 8,029,551 B2 | Page 1 of 1 |
| APPLICATION NO. | : 11/328619 | |
| DATED | : October 4, 2011 | |
| INVENTOR(S) | : Donald E. Running | |

It is certified that error appears in the above-identified patent and that said Letters Patent is hereby corrected as shown below:

Claim #22 - at Column 16 - Line 26: insert -- any -- before the word "movement"

Signed and Sealed this
Twenty-ninth Day of November, 2011

David J. Kappos
*Director of the United States Patent and Trademark Office*